(12) United States Patent
Wells et al.

(10) Patent No.: US 8,818,734 B1
(45) Date of Patent: Aug. 26, 2014

(54) PEPTIDE LIGANDS FOR SPERM DNA FRAGMENTATION ASSAY

(76) Inventors: Dagan Wells, Oxford (GB); Jacques Cohen, New York, NY (US); George Pieczenik, Stockton, NJ (US)

( * ) Notice: Subject to any disclaimer, the term of this patent is extended or adjusted under 35 U.S.C. 154(b) by 0 days.

(21) Appl. No.: 13/300,195

(22) Filed: Nov. 18, 2011

(51) Int. Cl.
*G01N 33/50* (2006.01)
*G01N 33/58* (2006.01)

(52) U.S. Cl.
CPC ............... *G01N 33/50* (2013.01); *G01N 33/58* (2013.01); *G01N 33/5091* (2013.01)
USPC ........................................... 702/19; 530/328

(58) Field of Classification Search
None
See application file for complete search history.

(56) References Cited

U.S. PATENT DOCUMENTS

| 6,541,206 | B1 | 4/2003 | Huzar |
| 7,993,827 | B2 | 8/2011 | Berenguer |
| 8,278,413 | B2 * | 10/2012 | Bonny ........................... 530/300 |

OTHER PUBLICATIONS

Selivanova, Galina et al; "The single stranded DNA end binding site of p53 coincides with the c-terminal regulatory region." Nuc. Acids Res. (1996) 24(18) p. 3560-3567.*
Behmoaras, Tula et al; "A tryptophan containing peptide recognizes and cleaves DNA at apurinic sites." Nature (1981) 292, p. 858-859.*
Hupp, Ted R. et al; "Small peptides activate the latent sequence specific DNA binding function of p53." Cell (1995) 83 p. 237-245.*

* cited by examiner

*Primary Examiner* — James H Alstrum Acevedo
*Assistant Examiner* — Fred Reynolds
(74) *Attorney, Agent, or Firm* — George Pieczenik

(57) ABSTRACT

This invention comprises peptides, methods and a kit for identifying DNA fragmentation in non-viable sperm. Specific peptide sequences are claimed that bind to ssDNA and fragmented DNA.

Figure 2:
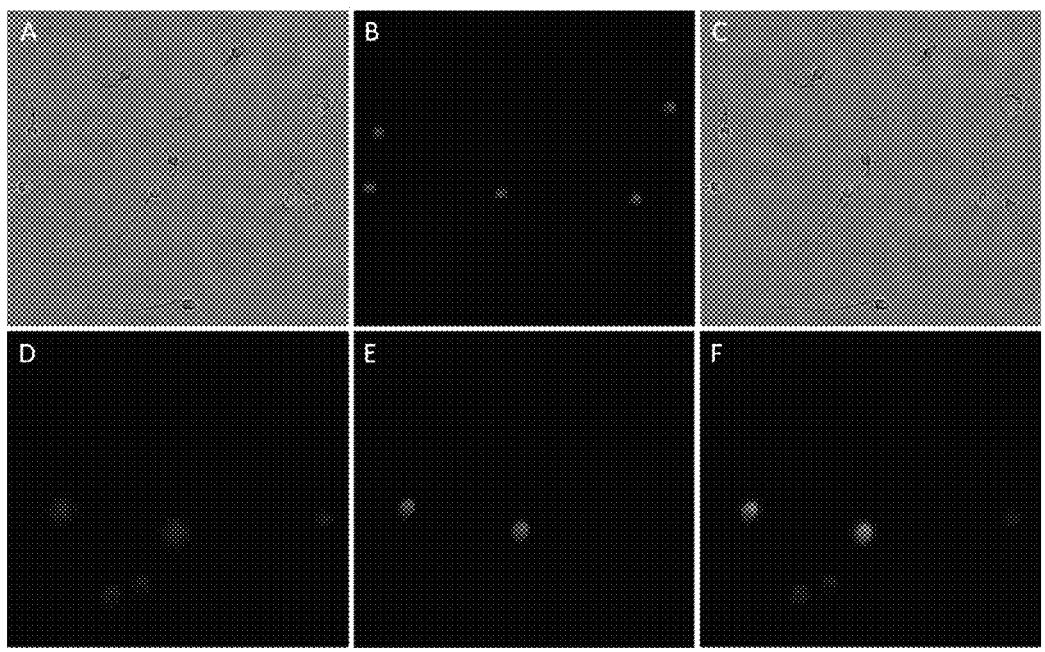

6 Claims, 7 Drawing Sheets
(6 of 7 Drawing Sheet(s) Filed in Color)

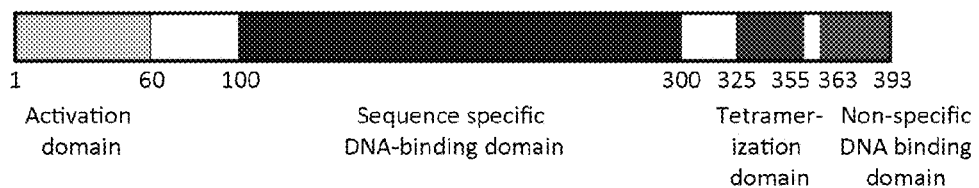

FIG.1

Domain organization of p53. Modified from Ahn & Prives (2001). p53 is a multidomain protein constituted by an N-terminal transcription-activation domain (TAD) that lies within residues 1-60, a central sequence-specific DNA-binding core domain (DBD) that lies within residues 100-300 and a multifunctional C-terminal domain that lies within residues 300-393. The p53 C-terminus can be subdivided further into three regions, a flexible linker (residues 300-320) that connects the DNA-binding domain to the tetramerization domain, the tetramerization domain itself (residues 325-355), and, at the extreme carboxyl terminus, a stretch of 30 amino acids that is rich in basic residues (residues 363-393).

(A-C) Human spermatozoa stained with DW1 (red). (A) Brightfield microscopy. (B) Fluorescence microscopy. (C) Combined image of brightfield and fluorescence microscopy.

(D-F) Human spermatozoa stained with DW1 (red) and DAPI (blue). (D) Blue (DAPI) channel (E) Red (DW1) channel (F) Red (DW1) and blue (DAPI) channels.

Human spermatozoa stained with DW1, Hoechst 33342 and FITC-PSA. (A) Red (DW1), blue (H342) and green (FITC-PSA) channels. (B) Blue (H342) channel. (C) Red (DW1) channel. (D) Green (FITC-PSA) channel. (E) Four staining patterns found in a sperm sample.

DW1 staining detection (%DW1 positive) and membrane integrity assessment (%PI negative) of 5 human sperm samples treated with increasing concentrations of ethanol.

SCDt processed spermatozoa. (A-C) Stained with DW1 (red) and DAPI (blue) (D-F) Stained with AO. AO binds to ssDNA emitting red fluorescence and to dsDNA emitting green fluorescence (G-H) ssDNA immunodetection using a FITC-labelled anti-ssDNA antibody (green) and DAPI (blue).

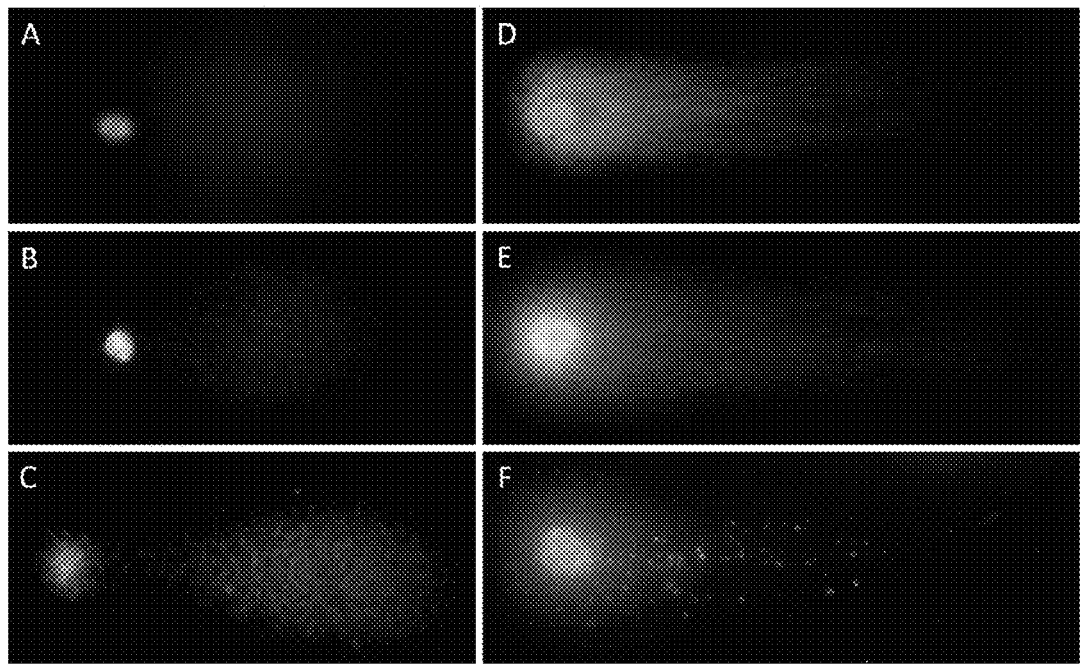

FIG. 6

(A-C) Alkaline comet assay-processed spermatozoa. (A) Stained with DW1 (red) and DAPI (blue) (B) Stained with AO. AO binds to ssDNA emitting red fluorescence and to dsDNA emitting green fluorescence (C) ssDNA immunodetection using a FITC-labelled anti-ssDNA antibody (green) and DAPI (blue). (D-F) Neutral comet assay-processed spermatozoa. (D) Stained with DW1 (red) and DAPI (blue) (E) Stained with AO. AO binds to ssDNA emitting red fluorescence and to dsDNA emitting green fluorescence (F) ssDNA immunodetection using a FITC-labelled anti-ssDNA antibody (green) and DAPI (blue).

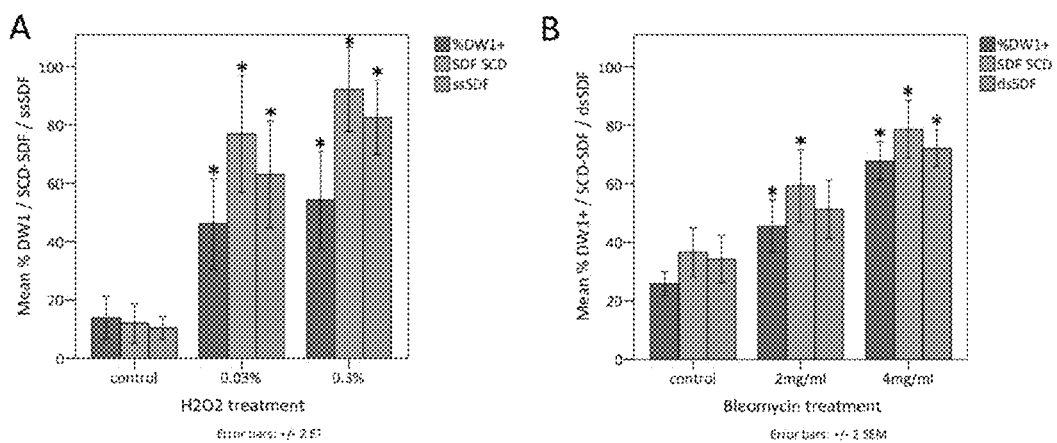

FIG. 7

DNA fragmentation detection by DW1 staining, SCDt and comet assay. (A) In 10 human sperm samples treated independently with $H_2O_2$. Groups significantly different to control (Dunnett's Test subsequent to ANOVA, $p<0.05$) are highlighted with an asterisk. (B) In 10 human sperm samples treated independently with Bleomycin. Groups significantly different to control (Mann-Whitney $U$ test, $p<0.05$) are highlighted with an asterisk.

PEPTIDE LIGANDS FOR SPERM DNA FRAGMENTATION ASSAY

SUMMARY

The integrity of DNA in spermatozoa is considered an additional parameter of semen quality and a potential fertility predictor. Significant progress has been made in recent years towards the development of reliable tests for sperm chromatin integrity and DNA damage assessment. However, most of the techniques available are either labor-intensive, require expensive instrumentation, or utilize enzymes whose activity could be compromised by the highly condensed nature of sperm chromatin. In addition, all the methods currently available involve the destruction of the sperm tested; none is able to select intact spermatozoa that could then be used for fertilization. The present invention application describes a peptide-ligand-based stain, capable of binding specific DNA structures, thereby revealing the presence of DNA damage, preferably in living cells.

The peptide products claimed in this invention were bioinformatically modeled on the critical region of the p53 protein associated with DNA binding and fluorescently labeled with a terminal rhodamine B dye. The ability of these synthetic peptides to detect DNA damage in intact and fixed human spermatozoa was assessed in detail. Human sperm samples were treated with active producers of single and double strand DNA breaks (hydrogen peroxide and bleomycin), and their effects measured by the peptide-stain and compared with other well established DNA damage evaluation tests such as the Comet assay and Sperm Chromatin Dispersion test (SCDt). The claimed peptides were confirmed to have a high affinity for single stranded DNA (ssDNA), DNA ends and other types of DNA lesions.

Additionally, the proportion of spermatozoa with intense staining was found to be closely associated with the percentage of cells possessing DNA damage, as determined using the SCDt and neutral and alkaline comet assays.

Therefore, we have invented novel viable peptide-based stains and methods capable of detecting DNA damage in individual cells. This invention's utility is as an inexpensive and simpler alternative to the conventional sperm DNA fragmentation assays. In addition, it differs from previous assays for fragmentation in that it does not damage viable non-fragmented sperm. It is a viable assay for sperm integrity.

BACKGROUND

Provisional Patent Filings and Patents

The following Provisional U.S. Patents filed under 35 USC 111(b) are to be incorporated by reference and to which this Non-Provisional Patent application claims priority under 35 USC 119(e). They are U.S. 61/415,419 filed Nov. 19, 2010 and U.S. 61/415,406 filed Nov. 19, 2010. In addition, the Pieczenik U.S. Pat. No. 5,866,363 is to be incorporated by reference, as a method of making combinatorial library variations of the peptide ligands claimed in this invention.

BACKGROUND OF THE INVENTION

1. Field of the Invention

The field of Invention is a product and method that are a viable biochemical test for the integrity of sperm DNA as a measure of semen quality and as a potential fertility predictor. This invention allows for selecting sperm that shows minimal DNA fragmentation. It comprises products, ligands, methods and a kit for identifying DNA fragmentation in viable sperm, inter alia.

2. Prior Art

Traditionally, the diagnosis of male infertility has been based on the assessment and analysis of spermatozoa concentration, motility and morphology. Although much progress has been made in the understanding of sperm physiology and interaction with the oocyte, these measures continue to be the most important and widely used means of evaluating male factor infertility. However, it is widely accepted that semen parameters convey only a limited degree of prognostic and diagnostic information. Conventional semen analysis is unable to detect the presence of subtle alterations in spermatozoa that might affect functionality. Therefore, there is a need for new markers allowing improved discrimination of sperm samples of high and low quality, and capable of providing a more accurate prediction of the likelihood of pregnancy and of miscarriage risk. Enhanced sperm evaluation may be of particular importance for the treatment of infertility.

Huszar's U.S. Pat. No. 6,541,206 describes a surface protein binding method for the assessment of sperm quality but requires that the sperm sample being tested be non-viable and it does not test the integrity of the sperm's DNA and chromatin structure.

Berenguer's U.S. Pat. No. 7,993,827 describes a method for the determination of DNA fragmentation in animal sperm. It refers to a procedure to evaluate the integrity of the chromatin/DNA of the sperm a DNA denaturing solution, but not a protein denaturing solution, followed, by a stain.

During the last 15 years, sperm DNA integrity has been considered an additional parameter of semen quality and a potential fertility predictor. Some studies indicate that DNA damage is associated with anomalies in the conventional semen parameters (Acharyya et al., 2005; Irvine et al., 2000). Others, however, have shown that sperm DNA integrity is independent from these parameters and suggest that its evaluation could provide valuable additional information (Giwercman et al., 2003). Sperm DNA damage has been recognized as a possible explanation of a high percentage of idiopathic infertility cases (Saleh et al., 2002). It has also been suggested that chromatin and DNA integrity are essential to ensure that the fertilizing spermatozoa can support the normal embryonic development of the zygote (Morris et al., 2002; Virro et al., 2004). Injecting spermatozoa with proven DNA integrity into human oocytes could be a useful therapeutic addition to ICSI treatment.

The exact mechanism by which sperm DNA fragmentation is produced is still unknown, however, several possible origins have been proposed. It could be the result of aberrant chromatin packaging during spermiogenesis (Marcon and Boissonneault, 2004; McPherson and Longo, 1993); a consequence of defective apoptosis of abnormal spermatozoa prior to ejaculation (Gorczyca et al., 1993b; Sakkas et al., 2002); induced by the excessive production of reactive oxygen species (ROS) in the ejaculate (Aitken et al., 1998; Kodama et al., 1997); and/or the result of other factors such as high temperature (Oliva et al., 2001), environmental or industrial toxic chemical compounds (Rubes et al., 2005), tobacco (Potts et al., 1999), caffeine (Schmid et al., 2007), advanced age (Wyrobek et al., 2006) or obesity (Kort et al., 2006). All these mechanisms may also be involved in abnormal spermiograms. Many studies have been performed in order to assess the significance of sperm DNA fragmentation and its impact on human reproduction. Although it remains a controversial issue, several studies have indicated that sperm DNA damage has a negative impact on conception for both natural (Evenson and Wixon, 2008) and assisted reproductive treatment (ART) cycles (Larson et al., 2000).

In in vitro fertilization (IVF), recent reports confirm that fertilisation rate is negatively correlated with sperm DNA fragmentation (Huang et al., 2005) and that it has a negative impact on pregnancy rates (Benchaib et al., 2007; Borini et al., 2006). In the case of intracytoplasmic sperm injection (ICSI), some studies have found that sperm DNA damage is inversely related to fertilization rate (Lopes et al., 1998) and that it negatively influences the implantation rate of embryos obtained by this technique (Benchaib et al., 2003; Larson-Cook et al., 2003). Moreover, sperm DNA fragmentation has been also associated with high miscarriage rate (Zini and Sigman, 2009)

Significant progress has been made towards the development of reliable tests for sperm chromatin integrity and DNA damage assessment. Methods include: Sperm Chromatin Structure assay (SCSA) (Evenson and Jost, 1994); Terminal deoxynucleotidyl transferase-mediated deoxyUridine triphosphate-Nick End Labeling (TUNEL) assay (Gorczyca et al., 1993a); Single-Cell Gel Electrophoresis (SCGE) or Comet Assay (Ostling and Johanson, 1984); and Sperm Chromatin Dispersion test (SCDt) (Fernandez et al., 2003). However, most of the techniques available for the evaluation of sperm DNA integrity are either labor-intensive, require expensive instrumentation, or necessitate the use of enzymes whose activity and accessibility could be compromised by the highly condensed sperm chromatin (SCGE/comet assay, SCSA or TUNEL, respectively). Some of these procedures are more suited to the research field than a clinical andrology laboratory. The SCDt does not require expensive instrumentation and is much simpler than the alternative techniques mentioned above, but even this straightforward method is still time-consuming and has therefore been difficult to incorporate in the demanding routine of an andrology/IVF laboratory.

In addition to these drawbacks, one of the most important limitations of all methods for the assessment of sperm DNA fragmentation is that none is able to select spermatozoa that could subsequently be used for fertilisation. All the techniques currently available involve the destruction of the sperm tested. The proportion of spermatozoa with fragmented DNA in a sample is revealed, but none of those that have been tested are viable following analysis. It is obvious that for the creation of a healthy embryo, only one viable spermatozoon is needed per oocyte. Therefore, a method allowing sperm to be tested for DNA fragmentation, while maintaining their viability, could allow poor quality samples to be rescued. Spermatozoa with intact DNA could be identified and selectively used for fertilization via ICSI, even if they only represented a small minority of the total sperm population. Such an approach could also be desirable in the case of good quality sperm samples, allowing fertilization with the best quality spermatozoa to be ensured. This may be particularly useful for cases in which few oocytes have been produced and fertilization with abnormal spermatozoa must be avoided at all costs. If desired, a test of this type could also be used to screen large populations of spermatozoa in the same way as the existing SCSA, SCGE/comet, TUNEL and SCDt methods.

In the present study we propose the use of inexpensive peptide-ligand-based stains that target DNA damage indicators. Short synthetic peptides can be designed to mimic certain protein domains that bind to specific epitopes (Merrifield, 2001). The design of short peptide sequences involves a variety of bioinformatic approaches, based on analysis of three-dimensional protein structure and/or known interacting peptide sequences (e.g. derived from well characterized antibodies, enzyme active sites or protein binding sites, etc). In most cases, peptides of this type do not have any impact on cell viability when used in vivo to target living cells (Pasqualini and Ruoslahti, 1996; Pieczenik et al., 2006).

A well-known molecule, with DNA binding properties, p53, was selected to be the focus for the development of peptides for detection of DNA lesions. p53 is a well-defined tumor suppressor protein that regulates the cell cycle and maintains the genomic integrity of the cell by orchestrating a wide variety of pathways involved in repair, apoptosis and senescence (Vogelstein et al., 2000). A three dimensional crystal structure shows a region at towards the C-terminus of the p53 protein which is able to bind to a wide variety of DNA structures including: single strand DNA ends (Bakalkin et al., 1994), short single DNA strands (Bakalkin et al., 1995), irradiated or enzymatically damaged DNA (Reed et al. 1995), four-way junctions (Lee et al., 1997), and insertion/deletions (Lee et al., 1995). The ability of p53 C-terminus to bind to ends, single strands gaps and other types of DNA lesions led us to propose that a synthetic oligopeptide designed to mimic the p53 C-terminal non-specific-sequence DNA-binding domain may directly recognize and bind damaged DNA. These damaged ends would appear in fragmenting DNA.

A twenty two amino acid chromophore labeled oligopeptide (DW1 (SEQ ID NO:1)), one of the peptide products of this invention and both modeled on the critical region of the p53 C-terminus associated with DNA binding, was used to assess the ability of, to detect DNA damage in human spermatozoa. Labeled forms of this peptide when applied to sperm samples have allowed sperm carrying high levels of DNA damage to be distinguished from those with low or no DNA damage. Furthermore, it is also possible to undertake this analysis without destruction of the cells tested, representing a viable stain for DNA integrity.

DEFINITIONS

ART: Assisted Reproductive Treatment AO: Acridine Orange; B: Blue-type sperm; DAPI: 4',6-Diamidino-2-Phenylindole DNA Deoxyribonucleic Acid; DNA: deoxyribonucleic acid, ds: double strand, DSB: double strand breaks, EB: ethidium bromide, FSC: Forward-Scatter Channel, ICSI-Intra Cytoplasmic Sperm Injection, IntDen: Integrated Density, IVF: In Vitro Fertilisation, Perim: Perimeter, RNA: Ribonucleic Acid, R: Red-type sperm, RB: RedBlue-type sperm, SCDt: Sperm Chromatin Dispersion test SCGE: Single Cell Gel Electrophoresis, SCSA: Sperm Chromatin, Structure Assay SDF: Sperm DNA Fragmentation index ss: single strand, SSC: Side-Scatter Channel, TBE: Tris-borate-EDTA buffer, TUNEL Terminal deoxynucleotidyl transferase-mediated deoxyUridine triphosphate-Nick End Labeling. Chromophore: rhodamine B, FITC, Fluorescein, procion dyes, inter alia.

DW1 (SEQ ID NO:1)-labeled peptide; rhodamine B-GSRAHSSHLKSKKGQSTSRHKK-COOH

DW2 (SEQ ID NO:2)-labeled peptide; rhodamine B-KGQSRSRHKK-COOH

| Amino acid abbreviations: | | |
|---|---|---|
| amino acid | three letter code | single letter |
| glycine | Gly | G |
| alanine | Ala | A |

-continued

| Amino acid abbreviations: | | |
|---|---|---|
| amino acid | three letter code | single letter |
| valine | Val | V |
| leucine | Leu | L |
| isoleucine | Ile | I |
| methionine | Met | M |
| phenylalanine | Phe | F |
| tryptophan | Trp | W |
| proline | Pro | P |
| serine | Ser | S |
| threonine | Thr | T |
| cysteine | Cys | C |
| tyrosine | Tyr | Y |
| asparagine | Asn | N |
| glutamine | Gln | Q |
| aspartic acid | Asp | D |
| glutamic acid | Glu | E |
| lysine | Lys | K |
| arginine | Arg | R |
| histidine | His | H |

EXAMPLES

Materials and Methods

Oligopeptide Design and Preparation:

Two synthetic oligopeptides (DW1 (SEQ ID NO:1)) corresponding to twenty one amino acid GSRAHSSHLK-SKKGQSTSRHKK) and KGQSRSRHKK (DW2 (SEQ ID NO:2)) ten amino acids of the human p53 carboxyl-terminal DNA binding domain and fluorescently labeled with a chromophore at its amino terminal rhodamine B dye was developed for the detection of DNA lesions. These oligopeptide were designed using a variety of bio-informatic approaches based on analysis of 3D protein structure. Specifically, the sequence corresponds to an exposed epitopic sequence in the single stranded DNA (ssDNA) binding region, deduced from the crystal structure of p53 binding to DNA and antibody binding to p53. Synthetic methods were the classical Merrifield peptide synthesis methods as referenced in the Pieczenik U.S. Pat. No. 5,866,363.

Semen Samples Collection

A total of 10 semen samples with normal conventional semen parameters according to the World Health Organization guidelines (WHO, 2010) were collected from couples undergoing ART treatment. Written consent for use of the sperm for research was obtained from patients.

Preparation of Agarose-Embedded Sperm Slides

Sperm samples were washed in PBS (220 g, 10 min) and diluted to a concentration of $10 \times 10^6$ spermatozoa/ml in phosphate-buffered saline (PBS, Fischer Scientific International, Pittsburgh, Pa. USA). Next, 25 µl of the cell dilution was mixed at 37° C. with 50 µl of 1% low melting point agarose (Sigma, St Louis, Mo., USA) previously liquefied at 90° C. An aliquot of 15 µl of the mixture was pipetted onto a glass slide pre-coated with 0.65% standard agarose, covered with a coverslip and transferred to an ice-cold metal plate to promote fast gelling. As soon as the gel solidified, coverslips were smoothly removed and the slides were used for direct DW1 (SEQ ID NO:1) staining, SCDt or comet assay.

SCD Test

The SCDt was performed using the Halosperm® kit (Halotech, Madrid, Spain). Sperm cells included in a microgel slide as described above, were submerged in an unwinding solution (80 µl of the acid denaturation solution provided in the kit in 10 ml of distilled water) for 7 min. The slides were then horizontally immersed in 10 ml of lysing solution B (provided in the kit) for 25 min. Finally, the slides were washed 5 min in abundant distilled water, dehydrated in increasing ethanol baths (70%-90%-100%, Sigma, St Louis, Mo., USA) for 2 min each, and air dried. All the incubations were carried out at room temperature.

Slides could be immediately analysed or stored at room temperature in the dark until needed. DNA was stained with either DAPI combined with Vectashield (125 ng/ml, Abbott Molecular Inc., Des Plaines, Ill., USA), DW1 (SEQ ID NO:1) oligopeptide (described below) or acridine orange (AO) (described below). The frequency of sperm cells with fragmented DNA, i.e. the Sperm DNA Fragmentation index (SDF), was established by measuring at least 500 sperm cells per slide. Sperm cells were classified as undamaged or damaged cells according to the patterns established by Fernandez et al. (2005).

Alkaline Comet Assay

Sperm cells included in a microgel slide as described above were submerged sequentially in two lysing solutions: lysing solution 1 [0.4 mol/l Tris-HCl (Sigma, St Louis, Mo., USA), 0.5 mol/l dithiothreitol (DTT, Sigma, St Louis, Mo., USA), 1% sodium dodecyl sulphate (SDS, Fluka, St Louis, Mo., USA), pH 7.5] for 30 min, followed by lysing solution 2 [0.4 mol/l Tris-HCl (Sigma, St Louis, Mo., USA), 2 mol/l NaCl (SAFC Biosciences, Lenexa, Kans., USA), 1% SDS (Fluka, St Louis, Mo., USA), 0.05 mol/l EDTA (Sigma, St Louis, Mo., USA), pH 7.5)] for 30 min. Then, slides were rinsed in TBE buffer (Fischer Scientific International, Pittsburgh, Pa., USA) for 10 min, washed in 0.9% NaCl (SAFC Biosciences, Lenexa, Kans., USA) and unwound in an alkaline solution [0.03 mol/l NaOH (Fluka, St Louis, Mo., USA), NaCl 1 mol/l (SAFC Biosciences, Lenexa, Kans., USA)] for 2.5 min. Slides were then transferred to a submerged horizontal gel electrophoresis cell (Bio-Rad, Richmond, Calif., USA) and electrophoresis performed at 20 V (1 V/cm), 40 mA for 4 min in 0.03 mol/l NaOH (Fluka, St Louis, Mo., USA). Finally, slides were rinsed once in neutralization buffer [(0.4 mol/l Tris-HCl, pH 7.5 (Sigma, St Louis, Mo., USA)] for 5 min, briefly washed in TBE buffer (Fischer Scientific International, Pittsburgh, Pa., USA), dehydrated in increasing concentrations of ethanol baths (70%-90%-100%, Sigma, St Louis, Mo., USA) for 2 minutes each, and air dried. All the incubations were carried out at room temperature. Slides could be immediately analysed or stored at room temperature in the dark until needed. DNA was stained with either DAPI combined with Vectashield (125 ng/ml, Abbott Molecular Inc., Des Plaines, Ill., USA), DW1 (SEQ ID NO:1) oligopeptide (described below) or AO (described below). The comets were assessed by visual scoring. The frequency of sperm cells with fragmented DNA, i.e. the Sperm DNA fragmentation index (SDF), was established by measuring at least 200 sperm cells per slide. Cells were classified as undamaged (no DNA migration) or ssDNA damaged (migrated DNA) cells as described by Enciso et al. (2009).

Neutral Comet Assay

Sperm cells included in a microgel slide as described above were submerged sequentially in two lysing solutions: lysing solution 1 [0.4 mol/l Tris-HCl (Sigma, St Louis, Mo., USA), 0.5 mol/l dithiothreitol (DTT, Sigma, St Louis, Mo., USA), 1% sodium dodecyl sulphate (SDS, Fluka, St Louis, Mo., USA), pH 7.5] for 30 min, followed by lysing solution 2 [(0.4 mol/l Tris-HCl (Sigma, St Louis, Mo., USA), 2 mol/l NaCl (SAFC Biosciences, Lenexa, Kans., USA), 1% SDS (Fluka, St Louis, Mo., USA), 0.05 mol/l EDTA (Sigma, St Louis, Mo., USA), pH 7.5)] for 30 min.

Then, slides were rinsed in TBE buffer (Fischer Scientific International, Pittsburgh, Pa., USA) for 10 min, transferred to a submerged horizontal gel electrophoresis cell (Bio-Rad, Richmond, Calif., USA) and immersed in fresh TBE electrophoresis buffer (Fischer Scientific International, Pittsburgh, Pa., USA). Electrophoresis was performed at 20 V (1 V/cm), 40 mA for 12.5 min. Afterwards, the slides were washed in 0.9% NaCl (SAFC Biosciences, Lenexa, Kans., USA), rinsed once in neutralization buffer [(0.4 mol/l Tris-HCl, pH 7.5 (Sigma, St Louis, Mo., USA)] for 5 min, briefly washed in TBE buffer (Fischer Scientific International, Pittsburgh, Pa., USA) and finally dehydrated in increasing concentrations of ethanol baths (70%-90%-100%, Sigma, St Louis, Mo., USA) for 2 minutes each, and air dried.

All the incubations were carried out at room temperature. Slides could be immediately analysed or stored at room temperature in the dark until needed. DNA was stained with either DAPI combined with Vectashield (125 ng/ml, Abbott Molecular Inc., Des Plaines, Ill., USA), DW1 (SEQ ID NO:1) oligopeptide, or AO (50 µM) (Aldrich, St Louis, Mo., USA).

The comets were assessed by visual scoring. The frequency of sperm cells with fragmented DNA, i.e. the Sperm DNA fragmentation index (SDF), was established by measuring at least 200 sperm cells per slide. Cells were classified as undamaged (no DNA migration) or double strand (ds) DNA damaged (migrated DNA) cells as described by Enciso et al. (2009). Sperm cells included in a microgel slide as described above were submerged sequentially in two lysing solutions: lysing solution 1 [0.4 mol/l Tris-HCl (Sigma, St Louis, Mo., USA), 0.5 mol/l dithiothreitol (DTT, Sigma, St Louis, Mo., USA), 1% sodium dodecyl sulphate (SDS, Fluka, St Louis, Mo., USA), pH for 30 min, followed by lysing solution 2 [(0.4 mol/l Tris-HCl (Sigma, St Louis, Mo., USA), 2 mol/l NaCl (SAFC Biosciences, Lenexa, Kans., USA), 1% SDS (Fluka, St Louis, Mo., USA), 0.05 mol/l EDTA (Sigma, St Louis, Mo., USA), pH 7.5)] for 30 min. Then, slides were rinsed in TBE buffer (Fischer Scientific International, Pittsburgh, Pa., USA) for 10 min, transferred to a submerged horizontal gel electrophoresis cell (Bio-Rad, Richmond, Calif., USA) and immersed in fresh TBE electrophoresis buffer (Fischer Scientific International, Pittsburgh, Pa., USA). Electrophoresis was performed at 20 V (1 V/cm), 40 mA for 12.5 min. Afterwards, the slides were washed in 0.9% NaCl (SAFC Biosciences, Lenexa, Kans., USA), rinsed once in neutralization buffer [(0.4 mol/l Tris-HCl, pH 7.5 (Sigma, St Louis, Mo., USA)] for 5 min, briefly washed in TBE buffer (Fischer Scientific International, Pittsburgh, Pa., USA) and finally dehydrated in increasing concentrations of ethanol baths (70%-90%-100%, Sigma, St Louis, Mo., USA) for 2 minutes each, and air dried.

All the incubations were carried out at room temperature.

Slides could be immediately analysed or stored at room temperature in the dark until needed.

DNA was stained with either DAPI combined with Vectashield (125 ng/ml, Abbott Molecular Inc., Des Plaines, Ill., USA), DW1 (SEQ ID NO:1) oligopeptide, or AO (50 µM) (Aldrich, St Louis, Mo., USA). The comets were assessed by visual scoring. The frequency of sperm cells with fragmented DNA, i.e. the Sperm DNA fragmentation index (SDF), was established by measuring at least 200 sperm cells per slide. Cells were classified as undamaged (no DNA migration) or double strand (ds) DNA damaged (migrated DNA) cells as described by Enciso et al. (2009).

Ethanol-Fixed Spermatozoa

Slides were prepared by smearing 40 µl of previously PBS-washed (220 g, 10 min) diluted sperm sample ($10 \times 10^6$ spermatozoa/ml) across the surface followed by air drying and fixation by immersion in ice-cold 95% ethanol (Sigma, St Louis, Mo., USA) for 5 min and air drying a second time.

Triton-X-100 Treated Spermatozoa

Fresh sperm suspensions were treated with Triton X-100 (Sigma-Aldrich, St Louis, Mo., USA) to permeabilize the plasma membranes (Kasai et al., 1999). An aliquot (400 µl) of fresh previously PBS-washed (220 g, 10 min) diluted sperm suspension ($10 \times 10^6$ spermatozoa/ml) was mixed with an equal volume of PBS (Fischer Scientific International, Pittsburgh, Pa., USA) containing 0.2% (w/v) Triton X-100 and agitated for 3 min. Then, 400 µl of PBS were added and the sperm cell suspension centrifuged for 10 min at 500 g. Pelleted spermatozoa were finally resuspended in 400 µl of PBS.

DW1 (SEQ ID NO:1) Staining

Fresh Spermatozoa in a Suspension

Briefly, 15 µl of previously PBS-washed (220 g, 10 min) diluted sperm suspension ($10 \times 10^6$ spermatozoa/ml) was exposed to 7.5 µl of DW1 (SEQ ID NO:1) ($1.25 \times 10^{-2}$ µg/ml) and immediately examined on a slide using an epifluorescence microscope (Olympus BX61, Hamburg, Germany). In certain cases, Hoechst 33342 (H342, 100 µg/ml, Sigma-Aldrich, St Louis, Mo., USA) was used as a counterstain for DNA.

Ethanol Fixed Spermatozoa

Slides were stained with DW1 (SEQ ID NO:1) at a concentration of $2.5 \times 10^{-3}$ mg/ml and immediately examined on a slide with an epifluorescence microscope (Olympus BX61, Hamburg, Germany). In certain cases, Hoechst 33342 (100 µg/ml, Sigma-Aldrich, St Louis, Mo., USA) was used as a counterstain for DNA.

Triton-X-100 Treated Spermatozoa

Briefly, 15 µl of sperm suspension was exposed to 7.5 µl of DW1 (SEQ ID NO:1) ($1.25 \times 10^{-2}$ µg/ml) and immediately examined on a slide with an epifluorescence microscope (Olympus BX61, Hamburg, Germany). In certain cases, Hoechst 33342 (H342, 100 µg/ml, Sigma-Aldrich, St Louis, Mo., was used as a counterstain for DNA.

Agarose-Embedded Spermatozoa

Unprocessed sperm, SCDt-processed and/or comet assay-processed slides were stained with freshly prepared $2.5 \times 10^{-3}$ mg/ml solution of DW1 (SEQ ID NO:1). A small amount (15 µl) of this peptide was added to a microgel slide containing spermatozoa, covered with a coverslip and immediately evaluated under epifluorescence microscope (Olympus BX61, Hamburg, Germany). In some cases, DAPI combined with Vectashield (125 ng/ml, Abbott Molecular Inc., Des Plaines, Ill., USA) was used as a counterstain for DNA.

Acridine Orange (AO) Staining

Unprocessed sperm, SCDt-processed and comet assay-processed slides were stained with freshly prepared AO stain ($0.5 \times 10^{-4}$ M, Sigma, St Louis, Mo., USA). Briefly, 15 µl of this solution was placed on a slide, covered with a coverslip and immediately evaluated under an epifluorescence microscope (Olympus BX61, Hamburg, Germany).

Membrane Integrity Assessment: Hoechst 33342/Propidium Iodide

To assess sperm membrane integrity, 15 µl of previously PBS-washed (220 g, 10 min) sperm suspension at a concentration of $10 \times 10^6$ spermatozoa/ml were exposed to 2.5 µl of H342 (100 µg/ml, Sigma-Aldrich, St Louis, Mo., USA) and 2.5 µl of Propidium Iodide (PI, 100 µg/ml, Sigma, St Louis, Mo., USA).

Each sample was then immediately evaluated under an epifluorescence microscope (Olympus BX61, Hamburg, Germany). Viable sperm were defined as those stained with H324 while resisting the uptake of PI; dead were defined as those sperm showing both PI and H342 fluorescence (Cai et al. 2005).

Acrosome Integrity FITC-PSA and Hoechst 33342

Acrosomal status was assessed using the acrosome-specific fluorochrome fluorescein isothiocyanate-labeled Pisum sativum agglutinin (FITC-PSA, Sigma, St Louis, Mo., USA). Briefly, 50 µl of previously PBS-washed (200 g, 10 min) sperm suspension ($10 \times 10^6$ spermatozoa/ml) was exposed to 2.5 µl of FITC-PSA (100 µg/ml, Sigma, St Louis, Mo., USA) and 2.5 µl H342 (100 µg/ml, Sigma, St Louis, Mo., USA) for 15 min at room temperature.

Spermatozoa were then examined with an epifluorescence microscope (Olympus BX61, Hamburg, Germany). Acrosomal status was assessed according to the staining patterns. Two patterns can be clearly identified: completely green acrosome fluorescence (intact acrosome), and no fluorescence or only a fluorescent band at the equatorial segment of the sperm head (reacted acrosome).

Acrosome Integrity and DNA Fragmentation Analysis FITC-PSA, Hoechst 33342 and DW1 (SEQ ID NO:1)

To simultaneously estimate sperm DNA fragmentation and acrosomal status, 50 µl of previously PBS-washed (220 g, 10 min) sperm suspension ($10 \times 10^6$ spermatozoa/ml) was exposed to 2.5 µl of FITC-PSA (100 µg/ml), 2.5 µL of H342 (100 µg/ml) and 7.5 µl of DW1 (SEQ ID NO:1) ($2.5 \times 10^{-3}$ mg/ml), gently mixed, incubated for 15 min at room temperature and then analysed under an epifluorescence microscope (Olympus BX61, Hamburg, Germany).

Single-Stranded DNA Immunodetection

Unprocessed sperm, SCDt-processed and neutral and alkaline comet assay-processed slides were neutralized (two washes of 400 mM Tris-HCl, pH 7.4, Sigma, St Louis, Mo., USA), drained and exposed to 50 µl of a mouse antibody specific to single-stranded DNA (10 µg/ml, Chemicon/Millipore, Schwalbach, Germany). Slides were then incubated overnight at 4° C. in a humidified atmosphere and subsequently washed three times with 5 ml of 100 mM Tris-HCl, pH 7.0 (Sigma, St Louis, Mo., USA). Afterwards, 50 µl of a secondary antibody (10 µg/ml, Biotinilated Rabbit Anti-mouse IgM, Jackson Immunoresearch Laboratories, West Grove, Pa., USA) was pipetted onto the agarose layer. Slides were incubated for 1 h at room temperature in a humidified atmosphere and washed three times as indicated. After washing, 50 µl of a third antibody (10 µg/ml, Alexa Flour 488 Streptavidin, Invitrogen, Carlsbad, Calif., USA) was pipetted onto the agarose layer and incubated at room temperature in a humidified atmosphere for 45 minutes (modified from Zhang et al. 2007). After washing, sperm nuclei were counterstained with DAPI (1 µg/ml, Sigma, St Louis, Mo., USA) and observed under an epifluorescence microscope (Olympus BX61, Hamburg, Germany).

Induction of Single-Strand DNA Damage: Hydrogen Peroxide (H2O2)

Five human sperm samples were washed in PBS (220 g, 10 min), diluted to a concentration of $10 \times 10^6$ spermatozoa/ml in PBS (Fischer Scientific International, Pittsburgh, Pa., USA) and divided into three aliquots of 200 µl each, allowing a control group to be compared with the treated cells. To induce single-strand DNA damage (Yamamoto, 1969), spermatozoa were incubated with 0.03 and 0.3% H2O2 (Sigma, St Louis, Mo., USA) for 30 min at room temperature. Next, SCDt, alkaline comet assay and DW1 (SEQ ID NO:1) staining of ethanol-fixed slides were performed.

Induction of Double-Strand DNA Damage: Bleomycin

Five human sperm samples were washed in PBS (220 g, 10 min), diluted to a concentration of $10 \times 10^6$ spermatozoa/ml in PBS (Fischer Scientific International, Pittsburgh, Pa., USA) and divided into three aliquots of 200 µl each, allowing a control group to be compared with the treated cells. To induce double-strand DNA damage, spermatozoa were incubated with 2 and 4 mg/ml of Bleomycin (Sigma, St Louis, Mo., USA) for 3 h at 37° C. (Povirk et al. 1989). Next, SCDt, neutral comet assay and DW1 (SEQ ID NO:1) staining of ethanol-fixed slides were performed.

Fluorescence Microscopy Evaluation and Image Capture

Slides were analyzed using a digital image analysis platform based on Olympus BX 61 fluorescence microscope (Olympus BX 61, Hamburg, Germany) equipped with a triple-band pass fluorescence filter block (for simultaneous visualisation of red, green and blue stains) and two single-band pass fluorescence filter block (red, rhodamine/TRITC; blue, DAR). Images were captured as tiff files using an Olympus digital camera and processed with Cytovision software (Genetix Ltd., Hampshire, UK).

Digital Image Analysis of DW1 (SEQ ID NO:1)-DAPI Stained Spermatozoa

The image processing software ImageJ (available at http://rsb.info.nih.gov/nih-imageJ; developed by Wayne Rasband, National Institutes of Health, Bethesda, Md., USA) was used for the quantification of red (DW1 (SEQ ID NO:1)-rhodamineB) and blue (DAPI) fluorescence per sperm cell in each of the visually established sperm types: Red (DW1 (SEQ ID NO:1)+) and Blue (DW1 (SEQ ID NO:1)-) spermatozoa. Control, $H_2O_2$ (0.03% and 0.3%) and Bleomycin (2 and 4 mg/ml)-treated sperm samples were used for this purpose. Ten fields per sample were captured as described above in the Fluorescence microscopy evaluation and image capture section using a fixed exposure time. A total of 300 sperm cells per slide were analysed.

The following parameters were considered for the quantitative measurement of Red (DW1 (SEQ ID NO:1)+) and Blue (DW1 (SEQ ID NO:1)-) sperm nuclei fluorescence: Area=area of the selection in square pixels, Mean grey value (Mean)=sum of the grey values of all the pixels in the selection divided by the number of pixels, Integrated Density (IntDen)=This is the sum of the grey values of the pixels in the selection.

This is equivalent to the product of the Area and Mean grey value.

Digital Image Analysis of DW1 (SEQ ID NO:1)-DAPI Stained SCDt Nucleoids

ImageJ was also used for the quantification of red (DW1 (SEQ ID NO:1)-rhodamine B) and blue (DAPI) fluorescence per nucleoid in a SCDt-processed control sample. A total of 20 nucleoids of each type (i.e with large or medium halo and with a small or no halo of dispersed DNA loops) were analysed. Images were acquired as described in the Fluorescence microscopy evaluation and image capture section using a fixed exposure time. The same quantitative measurement parameters described above (Area, Mean grey value and Integrated Density) were used as well to measure each sperm nucleoid blue and red fluorescence.

Digital Image Analysis of DW1 (SEQ ID NO:1)-DAPI Stained Alkaline and Neutral Comets ImageJ was also used for the quantification of red (DW1 (SEQ ID NO:1)-rhodamine B) and blue (DAPI) fluorescence per alkaline/neutral comet cell in a control sample. A total of 20 comets were analysed. Images were acquired as described in the Fluorescence microscopy evaluation and image capture section using a fixed exposure time. The same quantitative measurement parameters described above (Area, Mean grey value and Integrated Density) were used to measure each alkaline comet head and tail blue and red fluorescence.

Statistical Analyses

A Student t-test was used to compare the frequency of DW1 (SEQ ID NO:1)+ cells calculated in fresh and ethanol fixed samples. One way-ANOVA and Dunnett's Test for multiple comparisons with a single control were used to detect significant differences in the frequencies of DW1 (SEQ ID NO:1)+ sperm cells of samples treated with increasing concentrations of ethanol. These same tests were used to detect significant differences in the frequencies of H342/PI− sperm cells of samples treated with increasing concentrations of ethanol.

Pearson correlation coefficient was used to examine the relationship between the frequency of DW1 (SEQ ID NO:1)+ sperm cells and the percentage of membrane intact spermatozoa in samples treated with increasing concentrations of ethanol.

One way-ANOVA and Dunnett's Test for multiple comparisons with a single control were used to detect significant differences in the frequencies of SDF calculated by SCDt and alkaline comet assay between the control and each one of the treatments, 0.03% and 0.3% H2O2. The same test was performed to detect differences in the frequencies of DW1 (SEQ ID NO:1)+ sperm cells between the control and each one of the treatments, 0.03% and 0.3% $H_2O_2$. A Mann-Whitney U test was used to detect significant differences in the frequencies of SDF calculated by SCDt and neutral comet assay between the control and each one of the treatments, 2 mg/ml and 4 mg/ml of bleomycin. The Mann-Whitney U test was also performed to detect differences in the frequencies of DW1 (SEQ ID NO:1)+ sperm cells between the control and each one of the treatments, 2 mg/ml and 4 mg/ml of bleomycin. To determine significant differences in the values of each of the calculated parameters by the digital image analysis software ImageJ from the different DW1 (SEQ ID NO:1)-DAPI staining sperm types, a Kruskal-Wallis analysis was used. To determine these same differences in the different DW1 (SEQ ID NO:1)-DAPI staining SCDt nucleoids, a Student t-test analysis was used. To determine these differences in the case of the different DW1 (SEQ ID NO:1)-DAPI staining sperm types in H2O2-treated and Bleomycin-treated slides, a Mann-Whitney U test was used.

Pearson correlation coefficients were used to examine the relationship between the alkaline and neutral comet blue fluorescence (DAPI) parameters and the alkaline and neutral comet red fluorescence (DW1 (SEQ ID NO:1)) parameters calculated by ImageJ. Bivariate correlations between proportions of sperm cells with abnormal DNA integrity as detected by DW1 (SEQ ID NO:1)-DAPI staining test (% DW1 (SEQ ID NO:1)+) and the SDF values calculated by the SCDt were calculated with Pearson correlation coefficient.

All calculations were performed using SPSS v.14.0 (SPSS Inc., Chicago, Ill., USA) and one-tail p value<0.05 was considered significant.

Results

Staining of Fresh Spermatozoa in a Suspension.

When fresh intact spermatozoa in suspension were exposed to DW1 (SEQ ID NO:1), it was clear that the peptide was capable of binding to a subpopulation of the spermatozoa (FIG. 2). It was also apparent that the peptide bound to the posterior part of the sperm head, where the sperm DNA is located. No signal corresponding to DW1 (SEQ ID NO:1) could be seen in the tail. Binding of the peptide was apparently instantaneous at room temperature and persisted indefinitely (up to 24 hours was tested).

The combination of rhodamine labeled DW1 (SEQ ID NO:1) (red) and the DNA specific fluorochrome DAPI (blue) showed distinct staining patterns among different sperm nuclei. Some nuclei were entirely blue (DW1 (SEQ ID NO:1)−) and others red and blue (DW1 (SEQ ID NO:1)+), providing further evidence that DW1 (SEQ ID NO:1) staining is specific for DNA and that spermatozoa differ in the degree of peptide binding, perhaps due to differences in levels of DNA damage (FIG. 2D-F). The staining process was found to be compatible with continued sperm motility for at least 15 minutes.

However, it was noted that none of the motile spermatozoa exhibited DW1 (SEQ ID NO:1) staining. The spermatozoa showing peptide labeling were restricted to a subset of the immotile sperm. This result suggested that the staining may be dependent, not only on DNA damage, but also on sperm viability or perhaps membrane integrity. To confirm this possibility, an experiment to permeabilize the plasma membrane allowing the peptide to have access to the nucleus was designed (results are shown below). Additionally, we visualized the acrosome to assess whether the difference in staining could be related to membrane changes associated with the acrosome reaction.

Analysis of Peptide Staining of Acrosome Reacted Spermatozoa

When DW1 (SEQ ID NO:1) was used in combination with a nucleus-specific fluorochrome such as Hoechst 33342 and the acrosome specific stain FITC-PSA, the DNA-specificity of the oligopeptide was confirmed again. No DW1 (SEQ ID NO:1) signal could be seen in the acrosome (FIG. 3A-D). Four staining patterns were observed: green acrosome fluorescence and blue nucleus fluorescence (intact acrosome and DNA); green acrosome fluorescence and pink nucleus fluorescence (intact acrosome and damaged DNA); no green acrosome fluorescence and blue nucleus fluorescence (reacted acrosome, intact DNA); no green acrosome fluorescence and pink nucleus fluorescence (reacted acrosome and damaged DNA) (FIG. 3E). This suggests that the acrosome reaction does not influence the binding of DW1 (SEQ ID NO:1).

Staining of Ethanol-Fixed and Triton X-Treated Spermatozoa to Assess Peptide Staining in the Absence of the Plasma Membrane Ethanol fixation was used to remove sperm plasma membranes in order to ensure the access of DW1 (SEQ ID NO:1) to the nucleus in all cells, revealing whether differential membrane integrity could explain the various peptide staining patterns observed in the previous experiments. When ethanol-fixed spermatozoa were stained, binding to the posterior part of the sperm head, where the sperm nucleus is located was seen once again (FIG. 2). The proportion of DW1 (SEQ ID NO:1)-stained spermatozoa increased after fixation as compared to fresh samples (T-test, p<0.05; 32.30%±5.12% vs 23.40%±4.52%, respectively). Similar results were obtained when Triton-X was used to remove sperm plasma membranes.

Figure 4:
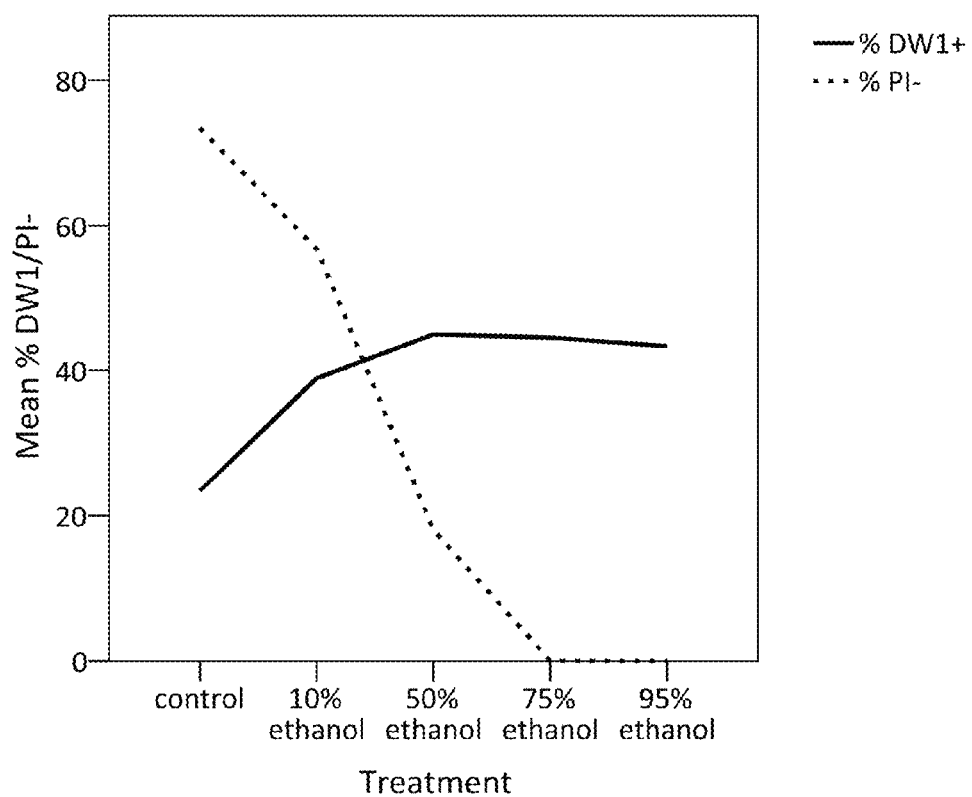

In another analysis, sperm plasma membranes were progressively permeabilised in a suspension containing increasing concentrations of ethanol. In this case, the percentage of DW1 (SEQ ID NO:1) stained spermatozoa significantly increased with ethanol concentration (Dunnett's Test subsequent to ANOVA, p<0.05) when 10, 50, 75 and 95% ethanol were used. No significant differences were found in the frequency of DW1 (SEQ ID NO:1)-labelled sperm cells between the samples exposed to 50, 75% and 95% ethanol. The increase in DW1 (SEQ ID NO:1) staining was consistent with a significant decrease (Dunnett's Test subsequent to ANOVA, p<0.05) in membrane integrity as assessed by the Hoechst 33342/PI assay (r=−0.752, Pearson correlation, p<0.01; FIG. 4). These experiments suggest that DW1 (SEQ ID NO:1)

specifically stains DNA, but cannot readily cross an intact plasma membrane. Similar results were obtained when increasing concentrations of Triton-X were used to disrupt or remove sperm plasma membranes.

What types of DNA does DW1 (SEQ ID NO:1) bind and can the peptide yield information on the extent of DNA damage?

Another important question concerns the forms of DNA for which the DW1 (SEQ ID NO:1) peptide has affinity. It was important to verify whether the peptide acts as a general DNA stain, or whether it has specificity for specific DNA structures, such as breaks and single strands. For this purpose, several different investigations were undertaken, as detailed below.

Staining of Spermatozoa Processed with the SCD Test

When DW1 (SEQ ID NO:1) was used to stain spermatozoa processed with the SCDt, results demonstrated no binding to the 'halo' of DNA around the core of the nucleoid, believed to represent undamaged loops of double stranded DNA. However, the peptide did bind to the core of all types of nucleoids generated by the assay: spermatozoa with large, small or no halo of dispersed DNA loops (FIG. 5A-C).

When the staining pattern was studied in detail with digital image analysis, a significantly higher level of DW1 (SEQ ID NO:1) staining was observed in spermatozoa containing high levels of DNA damage as assessed by the SCDt (i.e spermatozoa with a small or non-existent halo of dispersed DNA loops) compared to those defined by the SCDt as having intact DNA (i.e spermatozoa with a large or medium halo of dispersed DNA loops. Some of the parameters measured, in particular, Area (Red) and Integrated Density (Red) presented significantly higher values in spermatozoa with a small/no halo of dispersed DNA loops as compared to spermatozoa with large/medium haloes of dispersed DNA loops (T-test, p<0.05) (Table I). These results suggest that DW1 (SEQ ID NO:1) staining may indeed provide information about the DNA damage present in spermatozoa.

A similar pattern to that resulting from the staining with DW1 (SEQ ID NO:1) combined with DAPI could be observed in the SCDt nucleoids stained with AO (FIG. 5D-F). AO is a metachromatic dye that binds to ssDNA emitting red fluorescence and to dsDNA emitting green fluorescence. A similar distribution of an anti-ss antibody in SCDt nucleoids was observed as well (FIG. 5G-I). The similar distribution of DW1 (SEQ ID NO:1) fluorescence, AO red fluorescence and the anti-ss antibody observed suggests that DW1 (SEQ ID NO:1) binding sites might correspond to ssDNA.

Staining of Spermatozoa Processed with the Alkaline Comet Assay

When DW1 (SEQ ID NO:1) was used to stain spermatozoa processed with the neutral comet assay protocol, it bound to both the head and the tail of the neutral comet; however, when combined with DAPI, it479

When DW1 (SEQ ID NO:1) was used to stain spermatozoa processed with the alkaline comet assay, the fluorescently labeled oligopeptide bound to both the head and the tail of ssDNA fragments of the alkaline comet. However, when combined with DAPI, it was clear that the peptide had greatest affinity for the DNA fragments present in the comet tail (FIG. 6A).

When this staining pattern was studied in detail with digital image analysis, an inverse correlation (r=−0.501, Pearson correlation, p<0.05) between the amount of blue fluorescence (Integrated Density DAPI) in the comet head and the amount of red fluorescence (Integrated Density DW1 (SEQ ID NO:1)) in the comet tail of the alkaline comets analyzed was found. In addition, a positive significant correlation between the length/density of the tail (Area DAPI) and the level of DW1 (SEQ ID NO:1) staining in the alkaline comet (Integrated Density DW1 (SEQ ID NO:1)) was found (r=0.768, Pearson correlation, p<0.01). Those comets with longer/denser tails (i.e those nuclei presenting DNA damage) presented significantly higher levels of DW1 (SEQ ID NO:1) staining.

A similar pattern to that resulting from the staining with DW1 (SEQ ID NO:1) combined with DAPI can be observed in the alkaline comets stained with AO (FIG. 6B). A similar distribution of the anti-ss antibody used in the alkaline comets was observed as well (FIG. 6C). As in the case of the SCDt nucleoids, the similar distribution of DW1 (SEQ ID NO:1) fluorescence, AO red fluorescence and anti-ss antibody suggests that DW1 (SEQ ID NO:1) binding sites might correspond to ssDNA.

Staining of Spermatozoa Processed with the Neutral Comet Assay

It is clear that the peptide had greatest affinity of the terminal region of the comet tail (FIG. 6D). When this staining pattern was studied in detail with digital image analysis, a positive significant correlation between the length/density of the tail (Area DAPI) and the level of DW1 (SEQ ID NO:1) staining in the alkaline comet (Integrated Density DW1 (SEQ ID NO:1)) was found (r=0.835, Pearson correlation, p<0.01). Those comets with longer/denser tails (i.e those nuclei presenting DNA damage) presented significantly higher levels of DW1 (SEQ ID NO:1) staining.

A similar pattern to that resulting from the staining with DW1 (SEQ ID NO: 1) combined with DAPI can be observed in the neutral comets stained with AO (FIG. 6E). A similar distribution of the anti-ss antibody used in the neutral comets was observed as well (FIG. 6F). As in the case of the SCDt nucleoids and alkaline comets, the similar distribution of DW1 (SEQ ID NO:1) fluorescence, AO red fluorescence and anti-ss AB in neutral comets suggests that DW1 (SEQ ID NO:1) binding sites might correspond to ssDNA.

Induction of ssDNA Damage: Hydrogen Peroxide ($H_2O_2$)

In samples treated with $H_2O_2$, the percentage of cells positive for DW1 (SEQ ID NO:1) staining (DW1 (SEQ ID NO:1)+) significantly increased with $H_2O_2$ concentration (Dunnett's Test subsequent to ANOVA, p<0.05). A significant increase in the frequency of sperm cells with fragmented DNA detected by the SCDt (i.e SCDt-SDF) and the alkaline comet assay (i.e ssSDF), consistent with the increasing concentration of damaging agent, was also found (ANOVA, p<0.05; FIG. 7A). Not only did the number of DW1 (SEQ ID NO:1)+ cells increase after the treatment but also the intensity of DW1 (SEQ ID NO:1) staining per DW1 (SEQ ID NO:1)+ sperm cell was significantly higher, especially in the 0.3% $H_2O_2$-treated samples. Some of the parameters measured such as Area (Red), Mean grey value (Red) and Integrated Density (Red) presented significantly higher values in the Red-type cells found in the $H_2O_2$-treated samples compared to the ones of the control (Mann-Whitney U test, p<0.05) (Table II). These results indicate that DW1 (SEQ ID NO:1) may be detecting DNA damage, in particular the ssDNA breaks (SSBs) generated by $H_2O_2$.

Induction of dsDNA Damage: Bleomycin

In samples treated with Bleomycin, the frequency of sperm cells with fragmented DNA detected by the SCDt (i.e SCDt-SDF) and the neutral comet assay (i.e dsSDF) significantly increased with Bleomycin concentration (Mann-Whitney U test, p<0.05) (FIG. 7B). A significant increase in the percentage of red, DW1 (SEQ ID NO:1) positive, cell (% DW1 (SEQ ID NO:1)+), consistent with the increasing concentration of damaging agent, was also found (Mann-Whitney U test, p<0.05) (FIG. 7B). Not only did the number of DW1 (SEQ ID NO:1)+ cells increase after the treatment but also the intensity of DW1 (SEQ ID NO:1) staining per DW1 (SEQ ID NO:1)+ sperm cell was significantly higher especially in the 4 mg/ml Bleomycin-treated samples.

Some of the parameters measured such as Area (Red) and Mean (Red) presented significantly higher values in the Red-type cells found in the Bleomycin-treated samples (Mann-Whitney U test, p<0.05) (Table II). These results indicate that DW1 (SEQ ID NO:1) may be detecting DNA damage, in particular the dsDNA breaks (DSBs) generated by Bleomycin.

Finally, from the analysis of all the samples studied, we found that there is a significant and positive correlation between the percentage of DW1 (SEQ ID NO:1)+ sperm cells after DW1 (SEQ ID NO:1)-DAPI staining and the SDF calculated by the SCDt (r=0.789, Pearson correlation p<0.01). These results confirm that % DW1 (SEQ ID NO:1)+ sperm cells might give information about the degree of DNA damage present in a sperm sample.

Digital Image Analysis of DW1 (SEQ ID NO:1)-DAPI Stained Spermatozoa

In addition to visual scoring, digital image analysis was performed to produce a prototype for the automatic measurement of DNA damage by means of DW1 (SEQ ID NO:1) staining. Results from digital image analysis of 95% ethanol-fixed slides showed that the two sperm cell types (DW1 (SEQ ID NO:1)+ and DW1 (SEQ ID NO:1)−) were readily distinguishable. After image capture, ImageJ software was used to quantify red and blue fluorescence levels for each sperm type (Table III). Some of the parameters measured, in particular, Mean grey value (Red), Integrated Density (Red), Mean grey value (Red/blue) and Integrated Density (Red/blue) presented significantly different values in the two sperm types (Kruskal Wallis, p<0.05). This allowed the quantitative characterization of DW1 (SEQ ID NO:1)+ and DW1 (SEQ ID NO:1)− sperm types by digital image analysis.

LEGENDS FOR TABLES AND FIGURES

Table I. Image J measurement parameters calculated for each of the DW1 (SEQ ID NO:1)-DAPI staining SCDt nucleoid types.

TABLE I

Image J measurement parameters calculated for each of the DW1 ( SEQ ID NO: 1)-DAPI staining SCDt nucleoid types.

| Parameters | Large/Medium halo | Small/no halo |
|---|---|---|
| Area (Red) | 0.55 ± 0.04* | 0.71 ± 0.11* |
| Mean Grey value (Red) | 44.81 ± 5.22 | 58.82 ± 4.40 |
| Integrated Density (Red) | 22.82 ± 1.46* | 38.17 ± 5.57* |

TABLE II

Image J measurement parameters calculated for the DW1 (SEQ ID NO: 1)+ sperm type in control, $H_2O_2$-treated and Bleomycin-treated slides.

| Treatment | Area (Red) | Mean Grey value (Red) | Integrated Density (Red) |
|---|---|---|---|
| control | 0.21 ± 0.03 | 14.35 ± 1.37 | 3.55 ± 0.15 |
| 0.03% $H_2O_2$ | 0.24 ± 0.03* | 19.97 ± 2.10* | 3.64 ± 0.22 |
| 0.3% $H_2O_2$ | 0.30 ± 0.03* | 22.65 ± 2.42* | 3.62 ± 0.21 |
| 2 mg/ml Bleomycin | 0.23 ± 0.04 | 21.76 ± 2.58* | 3.66 ± 0.20 |
| 4 mg/ml Bleomycin | 0.28 ± 0.04* | 25.02 ± 0.04* | 3.37 ± 0.21 |

TABLE III

Image J measurement parameters calculated for each of the DW1 ( SEQ ID NO: 1)-DAPI staining sperm types in control slides.

| Parameters | Blue - type (DW−) | Red-type (DW+) |
|---|---|---|
| Area (Red) | 0.24 ± 0.02 | 0.26 ± 0.02 |
| Mean Grey value (Red) | 8.83 ± 1.09* | 15.08 ± 1.17* |
| Integrated Density (Red) | 1.77 ± 0.19* | 3.03 ± 0.16* |
| Area (Red/Blue) | 1.25 ± 0.13 | 1.40 ± 0.14 |
| Mean Grey value (Red/Blue) | 0.39 ± 0.04* | 0.67 ± 0.06* |
| Integrated Density (Red/Blue) | 0.43 ± 0.04* | 0.71 ± 0.04* |

Table II. Image J measurement parameters calculated for the DW1 (SEQ ID NO:1)+ sperm type in control, $H_2O_2$-treated and Bleomycin-treated slides.

Table III. Image J measurement parameters calculated for each of the DW1 (SEQ ID NO:1)-DAPI staining sperm types in control slides.

The patent or application file contains at least one drawing executed in color. Copies of this patent or patent application publication with color drawing(s) will be provided by the Office upon request and payment of the necessary fee.

FIG. 1. Domain organization of p53. Modified from Ahn & Prives (2001). p53 is a multidomain protein constituted by an N-terminal transcription-activation domain (TAD) that lies within residues 1-60, a central sequence-specific DNA-binding core domain (DBD) that lies within residues 100-300 and a multifunctional C-terminal domain that lies within residues 300-393. The p53 C-terminus can be subdivided further into three regions, a flexible linker (residues 300-320) that connects the DNA binding domain to the tetramerization domain, the tetramerization domain itself (residues 325-355), and, at the extreme carboxyl terminus, a stretch of 30 amino acids that is rich in basic residues (residues 363-393).

FIG. 2. (A-C) Human spermatozoa stained with DW1 (SEQ ID NO:1) (red). (A) Brightfield microscopy. (B) Fluorescence microscopy. (C) Combined image of brightfield and fluorescence microscopy. (D-F) Human spermatozoa stained with DW1 (SEQ ID NO:1) (red) and DAPI (blue). (D) Blue (DAPI) channel (E) Red (DW1 (SEQ ID NO:1)) channel (F) Red (DW1 (SEQ ID NO:1)) and blue (DAPI) channels.

Figure 3:
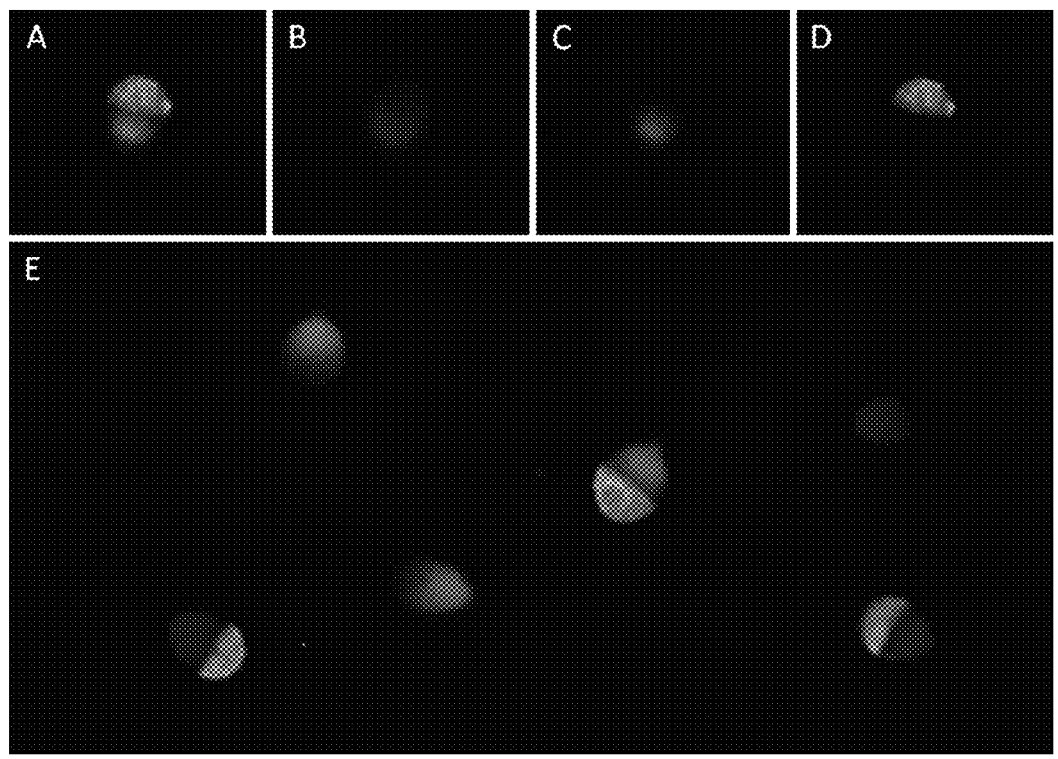

FIG. 3. Human spermatozoa stained with DW1 (SEQ ID NO:1), Hoechst 33342 and FITC-PSA. (A) Red (DW1 (SEQ ID NO:1)), blue (H342) and green (FITC-PSA) channels. (B) Blue (H342) channel. (C) Red (DW1 (SEQ ID NO:1)) channel. (D) Green (FITC-PSA) channel. (E) Four staining patterns found in a sperm sample.
160×114 mm (300×300 DPI)

FIG. 4. DW1 (SEQ ID NO:1) staining detection (% DW1 (SEQ ID NO:1) positive) and membrane integrity assessment (% PI negative) of 5 human sperm samples treated with increasing concentrations of ethanol. 160×128 mm (300×300 DPI)

Figure 5:
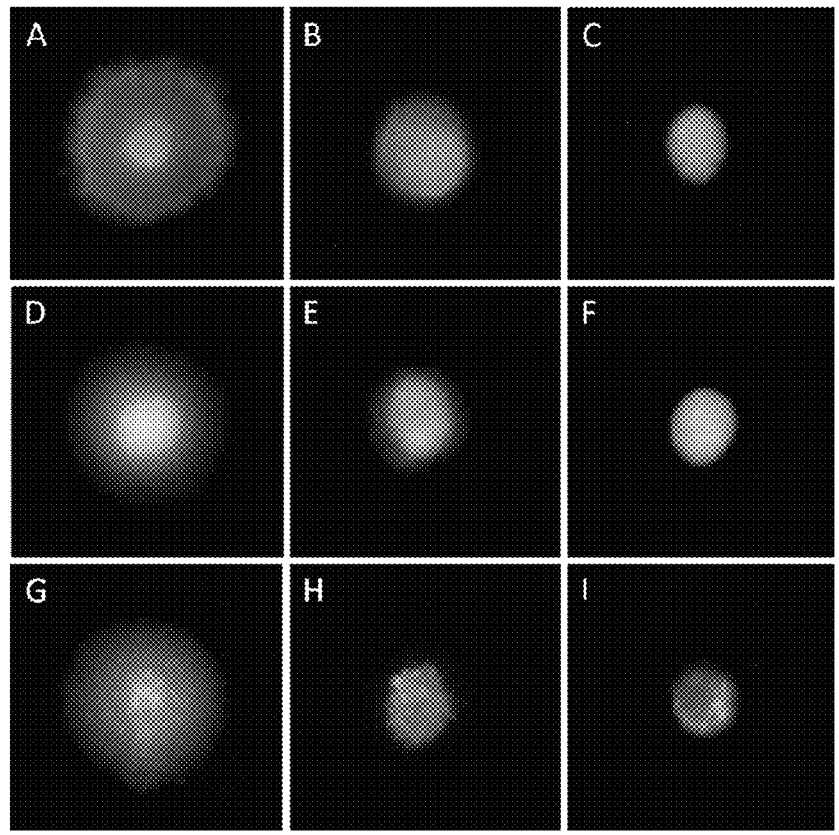

FIG. 5. SCDt processed spermatozoa. (A-C) Stained with DW1 (SEQ ID NO:1) (red) and DAPI (blue) (D-F) Stained with AO. AO binds to ssDNA emitting red fluorescence and to dsDNA emitting green fluorescence (G-H) ssDNA immunodetection using a FITC-labelled anti-ssDNA antibody (green) and
DAPI (blue). 127×127 mm (300×300 DPI)

FIG. 6. (A-C) Alkaline comet assay-processed spermatozoa. (A) Stained with DW1 (SEQ ID NO:1) (red) and DAPI (blue) (B) Stained with AO. AO binds to ssDNA emitting red fluorescence and to dsDNA emitting green fluorescence (C) ssDNA immunodetection using a FITC-labelled anti-ssDNA antibody (green)
and DAPI (blue). (D-F) Neutral comet assay-processed spermatozoa. (D) Stained with DW1 (SEQ ID NO:1) (red) and DAPI (blue) (E) Stained with AO. AO binds to ssDNA emitting red fluorescence and to dsDNA emitting green fluorescence (F) ssDNA immunodetection using a FITC-labelled anti-ssDNA antibody (green) and DAPI (blue).179×110 mm (300×300 DPI)

FIG. 7. DNA fragmentation detection by DW1 (SEQ ID NO:1) staining, SCDt and comet assay. (A) In 10 human sperm samples treated independently with H2O2. Groups significantly different to control (Dunnett's Test subsequent to ANOVA, p-0.05) are highlighted with an asterisk. (B) In 10 human sperm samples treated independently with Bleomycin. Groups significantly different to control
(Mann-Whitney U test, p<0.05) are highlighted with an asterisk.

DISCUSSION

The use of a novel peptide (DW1 (SEQ ID NO:1)) to stain spermatozoa in both a suspension and a fixed slide showed that the oligopeptide is nucleus-specific. The binding of DW1 (SEQ ID NO:1) to its corresponding binding sites in sperm occurred instantaneously, no incubation was required. Specific binding was easily achieved by simple adjustment of oligopeptide concentration. The peptide provided highly specific binding to the sperm nucleus at concentrations of $2.5 \times 10^{-3}$ mg/ml solution, although a wide range of additional concentrations were also found to be suitable. No binding was observed in either the tail or the acrosome confirming that DW1 (SEQ ID NO:1) has a high affinity for DNA. This was also confirmed in experiments in which the peptide was used to stain single stranded, double stranded and circular DNA ladders following electrophoresis on agarose gels (data not shown). Despite the affinity of DW1 (SEQ ID NO:1) for DNA, it seems that DW1 (SEQ ID NO:1) has specificity for particular DNA structures. When DW1 (SEQ ID NO:1) was combined with DAPI, the two dyes did not stain all regions of the nucleus with equal intensity. This indicates that DW1 (SEQ ID NO:1) and DAPI may have differences in their preferred binding sites.

We propose that DW1 (SEQ ID NO:1) is detecting certain specific DNA lesions while DAPI is detecting the whole DNA content of the sperm cell. This rationale is based on the increased DW1 (SEQ ID NO:1) staining seen in sperm samples exposed to genotoxic agents during this study (discussed below) and the fact that previous investigations have shown that the C-terminal domain of p53 specifically binds to irradiated or enzymatically damaged DNA (Reed et al., 1995), insertions/deletions (Lee et al., 1995) or four-way junctions (Lee et al., 1997). The affinity of DW1 (SEQ ID NO:1) for different DNA structures was explored in experiments performed on spermatozoa processed using established DNA damage detection techniques such as SCDt and comet assay. When DW1 (SEQ ID NO:1) was used to stain spermatozoa processed with the SCDt, results showed that it binds to the core of all the different types of nucleoids generated by the assay. However, spermatozoa with a small or no halo of dispersed DNA loops, defined by Fernandez et al (2003) as DNA-damaged spermatozoa, presented a significantly higher level of DW1 (SEQ ID NO:1) staining compared to spermatozoa with a large or medium halo of DNA loops, considered to represent intact DNA. The results suggest that DW1 (SEQ ID NO:1) staining is an indicator of DNA damage in sperm. The reason why damaged sperm processed with the SCDt lack DNA halos remains unknown.

However, it is clear that the absence of a halo is associated with the presence of large numbers of DNA breaks (Fernandez et al. 2003). It is thought that fragmented DNA remains trapped within the sperm head. The DNA breaks confined within the core of nucleoids appear to be detected by DW1 (SEQ ID NO:1). It is also possible that DW1 (SEQ ID NO:1) is detecting ssDNA sequences that have been denatured by the mild acid solution treatment used during the SCDt. The peptide does not stain the halo of DNA loops produced by the SCDt, considered to contain intact, undamaged DNA. Muriel et al. suggest that ssDNA regions in human spermatozoa may be a consequence of torsional constraints as a consequence of the tight packing requirements (Muriel et al., 2004). DW1 (SEQ ID NO:1) could also be detecting these structural constraints. More information about the behavior of DW1 (SEQ ID NO:1) and its affinity for certain DNA structures was obtained by staining spermatozoa processed with the neutral and alkaline versions of the comet assay. It is thought that neutral comet tails consist of extended DNA loops still attached to structures within the comet head, loop extension being produced by the presence of dsDNA breaks. In contrast, alkaline comet tails are not related to the chromatin loops, they are made up from ssDNA fragments produced by unwinding of the DNA at the break points (Afanasieva et al. 2010; Collins et al., 1997; Klaude et al., 1996).

In the case of neutral comets, the DW1 (SEQ ID NO:1) peptide was found to bind to the terminal region of the comet tails, which most likely represent the ends of broken DNA loops, providing a further indication that the peptide has an affinity for DNA ends. A strong DW1 (SEQ ID NO:1) binding can also be seen in the head of the comet, which might correspond to the ssDNA breaks present in the comet head, unable to migrate in electrophoretic neutral conditions. In the case of alkaline comets, DW1 (SEQ ID NO:1) binds to both the comet head and tail. In the alkaline protocol two types of DNA fragments are produced. DNA between closely spaced breaks in the same strand will unwind completely and become released as ssDNA fragments, forming a migrating tail/cloud during electrophoresis. If the breaks are far apart, the unwinding will cease before all DNA has become single stranded. Such fragments, only partially single stranded, are anchored in place by their contiguous double stranded regions and their exit from the comet head is further impeded by the high probability of entangling with other DNA molecules in the lysed nucleus (Klaude et al., 1996). The DW1 (SEQ ID NO:1) signal seen in the alkaline comet tail is consistent with our previous results, indicating that the peptide binds with high affinity to ssDNA fragments and DNA ends. Therefore, DW1 (SEQ ID NO:1) and DW2 (SEQ ID NO:2) can be defined as fragmented DNA binding peptides. The DW1 (SEQ ID NO:1) binding observed in the comet head might correspond to DNA ends and ssDNA gaps, left behind when ssDNA fragments migrated out of the nucleus, or to partially single stranded fragments unable to migrate from the head due to entanglement or due to the presence of dsDNA regions. When DAPI was used as a counterstain, a significant inverse correlation between the amount of DAPI fluorescence in the comet head and the amount of DW1 (SEQ ID NO:1) fluorescence in the comet tail was observed, as well as a positive significant correlation between the length/density of the tail and the level of DW1 (SEQ ID NO:1) staining in the comet. Given that the longer and denser the tail produced by the comet assay the greater the amount of DNA damage, this result also indicates that DW1 (SEQ ID NO:1) binding is associated with damaged DNA. A very similar pattern to that resulting from the combined staining with DW1 (SEQ ID NO:1) and DAPI was observed when AO was used to stain sperm treated using the SCDt, neutral or alkaline comet assays. AO is a selective methachromatic dye that interacts with DNA by intercalation or electrostatic attractions (Mitsuaki et al., 1971). When AO binds to dsDNA motifs, it intercalates in the DNA structure as a monomer, reaching a maximum emission at 525 nm (green). However, when AO binds to ssDNA it forms non-ordered aggregates where the maximum emission shifts to 650 nm (red) (Kasten, 1967). Hence, AO staining has the capacity to reveal the presence of both single stranded and double stranded DNA in the same nucleus. Comparison of DW1 (SEQ ID NO:1)-DAPI staining patterns and AO staining demonstrated a similar distribution of DW1 (SEQ ID NO:1) fluorescence and AO red fluorescence, suggesting that DW1 (SEQ ID NO:1) binding sites might correspond to ssDNA. Similar staining patterns to those observed with AO were found in the single-strand immunodetection assays performed on SCDt nucleoids, as well as neutral and alkaline comets, confirming the affinity of DW1 (SEQ ID NO:1) for ssDNA.

\This is an encouraging finding, since this property of the peptide is likely to be useful for the detection of ssDNA breaks in sperm nuclei. This characteristic of the DW1 (SEQ ID NO:1) peptide is consistent with the results of Jayaraman and Prives (1995), which suggest that the C-domain of p53 interacts with ssDNA, and with other studies showing that the C-terminus of p53 is capable of binding to ssDNA ends (Bakalkin et al., 1995; Selivanova et al., 1996). Taken together the data suggest that the DW1 (SEQ ID NO:1) peptide successfully mimics the ssDNA binding activity of p53. The fact that no motile spermatozoa presented DW1 (SEQ ID NO:1) staining might suggest that the peptide is unable to reach the nucleus of viable cells with intact membranes. Experiments permeabilizing the sperm plasma membrane showed that in ethanol-fixed and Triton-X treated spermatozoa stained with DW1 (SEQ ID NO:1), the binding of the oligopeptide to its corresponding binding sites occurred instantaneously and that the number of DW1 (SEQ ID NO:1)-positive spermatozoa was significantly higher compared with fresh samples. These results suggest that the permeabilization or removal of the membrane facilitates the access of the peptide to the DNA and that in viable sperm the integrity of the membrane prevents the peptide from entering the nucleus and recognizing DNA damage present.

Modification of DW1 (SEQ ID NO:1) to include a TAT peptide (YGRKKRRQRRRG), an amino acid sequence which has been shown to facilitate transduction of peptides or proteins into various cells, failed to improve access to the cell interior. However, it is possible that different TAT configurations or the use of an alternative protein transduction domain might allow penetration into the cell interior. Using ethanol fixed slides, DW1 (SEQ ID NO:1) peptide provided highly specific binding to the sperm nucleus at concentrations even lower than those used when sperm suspensions were stained ($2.5 \times 10^{-3}$ mg/ml solution). This finding supports the idea that DW1 (SEQ ID NO:1) needs the membrane to be permeabilized in order to reach the nucleus. Unfortunately this means that, at present, DW1 (SEQ ID NO:1) cannot be applied to distinguish spermatozoa with intact membranes that are free from DNA damage from those with intact membranes that are not. It is still possible that the peptide could be used to choose spermatozoa for fertilization using ICSI following removal of membranes using detergent. Previous studies have shown that sperm treated in this way remain fertilizations competent (Kasai et al., 1999). In addition, electroporation may allow DW1 (SEQ ID NO:1) and DW2 (SEQ ID NO:2) to enter sperm. Electroporation is known not to inhibit sperm viability and ICSI procedures.

Peptergents

In addition, there are a class of peptides called peptergents. They are sequences such as VVVVVVD or VVVVVVE. These sequences can be synthesized covalently to DW1 (SEQ ID NO:1) or DW2 (SEQ ID NO:2) (as amino end and/or the carboxyl end) or added separately as another peptide with DW1 (SEQ ID NO: 1) or 2.

This procedures is milder than electroporation.

However, more work will need to be done to assess any potential toxicity of this approach. Regardless of whether the peptide can be used for selection of individual spermatozoa, it is capable of providing a measure of the proportion of cells in a sperm sample affected by DNA damage. In membrane-free cells, treated with detergent or ethanol, DW1 (SEQ ID NO:1) staining successfully quantified the presence of DNA damage, indicating that the application of the peptide may be considered as a rapid and inexpensive alternative to the sperm DNA fragmentation detection tests in current use.

Furthermore, at higher concentrations DW1 (SEQ ID NO:1) can be used to assess sperm membrane integrity, thus revealing potentially viable cells that could be used for ICSI in a manner similar to Sybr14/Propidium Iodide testing. Experiments were undertaken with the aim of testing the ability of the peptide to detect DNA damage in a human semen sample (i.e. provide a population overview of damage levels), as well as its capacity to identify individual sperm containing DNA fragmentation. Results showed that the proportion of DW1 (SEQ ID NO:1)-positive sperm cells correlates with the proportion of spermatozoa possessing induced DNA damage of various kinds, as revealed by the SCDt, and the alkaline and neutral comet assays. These findings suggest, once again, that peptide staining is related to the presence of DNA damage in the sperm nuclei and that DW1 (SEQ ID NO:1) could be used to detect the amount of DNA damage present in a human sperm sample. The frequency of stained sperm cells increased as concentrations of $H_2O_2$ or Bleomycin were incrementally elevated, indicating that DW1 (SEQ ID NO:1) can quantify spermatozoa containing ss and ds DNA damage, respectively. Digital image analysis showed that not only the proportion of sperm positive for DW1 (SEQ ID NO:1) staining, but also the intensity of staining in individual cells (Integrated Density, IntDen DW1 (SEQ ID NO:1)), was associated with the amount of dsDNA and ssDNA damage.

In conclusion, this study shows that this invention, the novel synthetic DW1 (SEQ ID NO:1) peptide, has affinity for ssDNA, DNA ends or other types of DNA lesions. It has also been demonstrated that DW1 (SEQ ID NO:1) staining correlates with the results of other tests for sperm DNA and chromatin structure damage (SCDt, comet assay, etc). Unfortunately, current protocols do not allow the peptide to cross the plasma membrane preventing it from being used for the selection of healthy sperm with intact membranes without DNA damage for use in ICSI. Nevertheless, it can still be used to assess the level of DNA damage present in previously ethanol-fixed or Triton X-permeabilised spermatozoa and, as such, could represent a less expensive, fast and easier to use, alternative to existing methods of DNA damage evaluation in sperm samples. The peptide may also have value for the analysis and preferential selection for use in ICSI of viable sperm cells, since dead cells have DW1 (SEQ ID NO:1) permeable membranes and are therefore readily identified. Future work will focus on the development and optimization of plasma membrane permeable peptides targeting DNA damage, allowing application of this novel technique to viable spermatozoa.

There are several possibilities of combining several sperm dyes to create a kit that will allow for identifying viable sperm.

One example, is the following:

Annexin V detects phosphatydlserine on the surface of sperm plasma membrane.

Phosphatydlserine is an early surface marker for apoptosis (fragmentation of DNA and cell death). Annexin V is a $Ca^{2+}$-dependent phospholipid binding-protein that has a high affinity for phosphatydlserine. Annexin V can be labeled with various chromophores. One such chromophore which is a fluorescent moiety is Alexa Fluor 568 (red fluorescence, Molecular Probes).

Therefore, Annexin V can be used with nuclear stains such as DW1 and DW2 (SEQ ID NO:2) which serve as markers for cell permeability and DNA fragmentation. In addition, SYTOX green (S), a green-fluorescent dye that is impermeant to live cells, and Hoechst 33342 (H), a cell-permeant stain that emits blue fluorescence when bound to double stranded DNA. Thus, Annexin V stains sperm with phosphatydlserine in the outer leaflet of the plasma membrane (a sign of early apoptosis), Hoechst stains the sperm head of all sperm, and SYTOX only the head of non-viable sperm. It is thus possible to distinguish four sperm subpopulations in a sample: a) viable sperm (A−/S−/H+); (b) early apoptosis (A+/S−/H+); (c) late apoptosis (A+/S+/H+) and (d) necrosis (A−/S+/H+). To perform the assay a sperm suspension (100 μl) in culture medium is incubated with Annexin V (5 μl), SYTOX green (10 μl of a 5 nM solution) and Hoechst 33342 for 15 min at room temperature. The suspension is then centrifuged at 800×g for 10 min, the pellet mounted on a slide with mounting medium, and the sample observed with a fluorescence microscope.

Annexin V binds phosphatydlserine, a measure of apoptosis. It is used clinically in cardiac patients and in sperm assays. It doesn't bind viable or necrotic sperm (the two extremes), but it binds early apoptosis and late apoptosis, (that is when DNA starts to fragment and then membranes start to degrade). Whereas, DW1 (SEQ ID NO:1) and DW2 (SEQ ID NO:2) will stain one extreme-necrotic sperm (which has both permeable membranes and ssDNA). Therefore, the only sperm not stained with Annexin V and DW1 (SEQ ID NO:1) or DW2 (SEQ ID NO:2) will be viable sperm. Both are relatively non toxic and can be used to cell sort out the non-optimal sperm. Different chromophores can be attached so that there is no color or fluorescent overlap. Therefore, a kit of DW1 (SEQ ID NO:1) and/or DW2 (SEQ ID NO:2) and Annexin V should allow those sperm not stained to be used for ICSI and have a good chance of producing viable embryos.

Therefore, both DW1 (SEQ ID NO:1) and DW2 (SEQ ID NO:2) and Annexin V will make a useful kit for determining viable sperm for fertility procedures such as ICSI, inter alia.

REFERENCES

Acharyya S, Kanjilal S, Bhattacharyya A K. Does human sperm nuclear DNA integrity affect embryo quality? Indian J Exp Biol 2005; 43: 1016-1022.

Afanasieva K, Zazhytska M, Sivolob A. Kinetics of comet formation in single-cell gel electrophoresis: loops and fragments. Electrophoresis 2010; 31: 512-519.

Ahn J, Prives C. The C-terminus of p53: the more you learn the less you know. Nat Struct Biol 2001; 8: 730-732.

Aitken, R J. The Amoroso Lecture. The human spermatozoon—a cell in crisis?. J Reprod Fertil 1999; 115: 1-7.

Aitken R J, Gordon E, Harkiss D, Twigg J P, Milne P, Jennings Z, Irvine D S. Relative impact of oxidative stress on the functional competence and genomic integrity of human spermatozoa. Biol Reprod 1998; 59: 1037-1046.

Bakalkin G, Selivanova G, Yakovleva T, Kiseleva E, Kashuba E, Magnusson K P, Szekely L, Klein G, Terenius L, Wiman K G. p53 binds single-stranded DNA ends through the C-terminal domain and internal DNA segments via the middle domain. Nucleic Acids Res 1995; 23: 362-369.

Bakalkin G, Yakovleva T, Selivanova G, Magnusson K P, Szekely L, Kiseleva E, Klein 729 G, Terenius L, Wiman K G. p53 binds single-stranded DNA ends and catalyzes DNA renaturation and strand transfer. Proc Natl Acad Sci USA 1994; 91: 413-417.

Benchaib M, Braun V, Lornage J, Hadj S, Salle S, Lejeune H, Guerin J. Sperm DNA fragmentation decreases the pregnancy rate in an assisted reproductive technique. Hum Reprod 2003; 18: 1023-1028.

Benchaib M, Lornage J, Mazoyer C, Lejeune H, Salle B, Francois Guerin J. Sperm deoxyribonucleic acid fragmentation as a prognostic indicator of assisted reproductive technology outcome. Fertil Steril 2007; 87: 93-100.

Boivin J, Bunting L, Collins J A, Nygren K G. International estimates of infertility prevalence and treatment-seeking: potential need and demand for infertility medical care. Hum Reprod 2007; 22:1506-1512.

Borini A, Tarozzi N, Bizzaro D, Bonu M A, Fava L, Flamigni C, Coticchio G. Sperm DNA fragmentation: paternal effect on early post-implantation embryo development in ART. Hum Reprod 2006; 21: 2876-2881.

Cai K, Yang J, Guan M, Ji W, Li Y, Rens W. Single UV excitation of Hoechst 33342 and propidium iodide for viability assessment of rhesus monkey spermatozoa using flow cytometry. Arch Androl 2005; 51(5): 371-383.

Collins A R, Dobson V L, Dusinska M, Kennedy G, Stetina R. The comet assay: what can it really tell us? Mutat Res 1997; 375: 183-193.

Enciso M, Sarasa J, Agarwal A, Fernandez J L, Gosalvez J. A two-tailed Comet assay for assessing DNA damage in spermatozoa. Reprod Biomed Online 2009; 18(5): 609-616.

Evenson D, Jost L. Sperm chromatin structure assay: DNA denaturability. Methods Cell Biol 1994; 42: 159-176.

Evenson D P, Wixon R. Data analysis of two in vivo fertility studies using Sperm Chromatin Structure Assay-derived DNA fragmentation index vs. pregnancy outcome. Fertil Steril 2008; 90: 1229-1231.

Fernandez J, Muriel L, Rivero M, Goyanes V, Vazquez J, Alvarez J G. The sperm chromatin dispersion test: a simple method for the determination of sperm DNA fragmentation. J Androl 2003; 24: 59-66.

Gandini L, Lombardo F, Paoli D, Caruso F, Eleuteri P, Leter G. Ciriminna R, Culasso F, Dondero F, Lenzi A, Spano M. Full-term pregnancies achieved with ICSI despite high levels of sperm chromatin damage. Hum Reprod 2004; 19: 1409-1417.

Giwercman A, Richthoff J, Hjollund H, Bonde J P, Jepson K, Frohm B, Spano M. Correlation between sperm motility and sperm chromatin structure assay parameters. Fertil Steril 2003; 80: 1404-1412.

Gorczyca W, Gong J, Darzynkiewicz Z. Detection of DNA strand breaks in individual 777 apoptotic cells by the in situ terminal deoxynucleotidyl transferase and nick translation assays. Cancer Res 1993a; 53: 1945-1951.

Gorczyca W, Traganos F, Jesionowska H, Darzynkiewicz Z. Presence of DNA strand breaks and increased sensitivity of DNA in situ to denaturation in abnormal human sperm cells: analogy to apoptosis of somatic cells. Exp Cell Res 1993b; 207: 202-205.

Henkel R, Kierspel E, Hajimohammad M, Stalf T, Hoogendijk C, Mehnert C, Menkveld R, Schill W B, Kruger T F. DNA fragmentation of spermatozoa and assisted reproduction technology. Reprod Biomed Online 2003; 7: 477-484.

Huang C C, Lin D P, Tsao H M, Cheng T C, Liu C H, Lee M S. Sperm DNA fragmentation negatively correlates with velocity and fertilisation rates but might not affect pregnancy rates. Fertil Steril 2005; 84: 130-140.

Irvine D S, Twigg J P, Gordon E L, Fulton N, Milne P A, Aitken R J. DNA integrity in human spermatozoa: relationships with semen quality. J Androl 2000; 21: 33-44.

Jayaraman J, Prives C. Activation of p53 sequence-specific DNA binding by short single strands of DNA requires the p53 C-terminus. Cell 1995; 81: 1021-1029.

Kamel R M. Management of the infertile couple: an evidence-based protocol. Reprod Biol Endocrinol 2010; 8: 21.

Kasai T, Hoshi K, Yanagimachi R. Effect of sperm immobilisation and demembranation 802 on the oocyte activation rate in the mouse. Zygote 1999; 7(3): 187-193.

Kasten F H. Cytochemical studies with acridine orange and the influence of dye contaminants in the staining of nucleic acids. Int Rev Cytol 1967; 21: 141-202.

Klaude M, Eriksson S, Nygren J, Ahnstrom G. The comet assay: mechanism and technical considerations. Mutation Res 1996; 363: 89-96.

Kodama H, Yamaguchi R, Fukuda J, Kasai H, Tanaka T. Increased oxidative deoxyribonucleic acid damage in the spermatozoa of infertile male patients. Fertil Steril 1997; 68: 519-524.

Kort H I, Massey J B, Elsner C W, Mitchell-Leef D, Shapiro D B, Witt M A, Roudebush W E. Impact of body mass index values on sperm quantity and quality. J Androl 2006; 27: 450-452.

Larson-Cook K L, Brannian J D, Hansen K A, Kasperson K M, Aamold E T, Evenson D P. Relationship between the outcomes of assisted reproductive techniques and sperm DNA fragmentation as measured by the sperm chromatin structure assay. Fertil Steril 2003; 80: 895-902.

Larson K L, Dejonge C J, Barnes A M, Jost L K, Evenson D P. Sperm chromatin structure assay parameters as predictors of failed pregnancy following assisted reproductive techniques. Hum Reprod 2000; 15: 1717-1722.

Lee S, Cavallo L, Griffith J. Human p53 binds Holliday junctions strongly and facilitates their cleavage. J Biol Chem 1997; 272: 7532-7539.

Lee S, Elenbaas B, Levine A, Griffith J. p53 and its 14 kDa C-terminal domain recognize primary DNA damage in the form of insertion/deletion mismatches. Cell 1995; 81: 1013-1020.

Lewis S E. 2007. Is sperm evaluation useful in predicting human fertility? Reproduction 2007; 134: 31-40.

Lopes S, Sun J G, Jurisicova A, Meriano J, Casper R F. Sperm deoxyribonucleic acid fragmentation is increased in poor-quality semen samples and correlates with failed fertilisation in intracytoplasmic sperm injection. Fertil Steril 1998; 69: 528-532.

Marcon L, Boissonneault G. Transient DNA strand breaks during mouse and human spermiogenesis new insights in stage specificity and link to chromatin remodeling. Biol Reprod 2004; 70: 910-918.

McPherson S, Longo F. Chromatin structure-function alterations during mammalian spermatogenesis: DNA nicking and repair in elongating spermatids. Eur J Histochem 1993; 37: 109-128.

Merrifield B. Life during a Golden Age of Peptide Chemistry—The Concept and Development of Solid-Phase Peptide Synthesis. 2001. Oxford University Press, Oxford, UK.

Sakoda M, Hiromi K, Akasaka K. Kinetic studies of interaction between acridine orange and DNA. Biopolymers 1971; 10: 1003-1012.

Morris I D, Ilott S, Dixon L, Brison D R. The spectrum of DNA damage in human 852 sperm assessed by single cell gel electrophoresis (Comet assay) and its relationship to fertilisation and embryo development. Hum Reprod 2002; 17: 990-998.

Muriel L, Segrelles E, Goyanes V, Gosalvez J, Fernandez J L. Structure of human sperm DNA and background damage analysed by in situ enzymatic treatment and digital image analysis. Mol Hum Reprod 2004; 10: 203-209.

Oliva A, Spira A, Multigner L. Contribution of environmental factors to the risk of male infertility. Hum Reprod 2001; 16: 1768-1776.

Ostling O, Johanson K J. Microelectrophoretic study of radiation-induced DNA damages in individual mammalian cells. Biochem Biophys Res Commun 1984; 123: 291-298.

Pasqualini R, Ruoslahti E. Organ targeting in vivo using phage display peptide libraries. Nature 1996; 380: 364-366.

Pieczenik G, Garrisi J, Cohen J. Inhibition of human spermatozoa-zona pellucida binding by a combinatorially derived peptide from a synthetic target. Reprod Biomed Online 2006; 13: 361-367.

Potts R, Newbury C, Smith G, Notarianni L, Jefferies T. Sperm chromatin damage associated with male smoking. Mutation Res 1999; 423: 103-111.

Povirk L F, Han Y H, Steighner R J. Structure of bleomycin-induced DNA double-strand breaks: predominance of blunt ends and single-base 5' extensions. Biochemistry 1989; 28: 8508-8514.

Reed M, Woelker B, Wang P, Wang Y, Anderson M E. Tegtmeyer P. The C-terminal domain of p53 recognizes DNA damaged by ionizing radiation. Proc Natl Acad Sci USA 1995; 92: 9455-9459.

Rubes J, Selevan S G, Evenson D P, Zudova D, Vozdova M, Zudova Z, Robbins W A, Perreault S D. Episodic air pollution is associated with increased DNA fragmentation in human sperm without other changes in semen quality. Hum Reprod 2005; 20: 2776-2783.

Sakkas D, Moffatt O, Manicardi G C, Mariethoz E, Tarozzi N, Bizzaro D. Nature of DNA damage in ejaculated human spermatozoa and the possible involvement of apoptosis. Biol Reprod 2002; 66: 1061-1067.

Saleh R, Agarwal A, Nelson D, Nada E, El-Tonsy M, Alvarez E, Thomas A J, Sharma R. Increased sperm nuclear DNA damage in normozoospermic infertile men: a prospective study. Fertil Steril 2002; 78: 313-318.

Schmid T E, Eskenazi B, Baumgartner A, Marchetti F, Young S, Weldon R, Anderson D, Wyrobek A J. The effects of male age on sperm DNA damage in healthy non-smokers. Hum Reprod 2007; 22: 180-187.

Selivanova G, Iotsova V, Kiseleva E, Strom M, Bakalkin G, Grafstrom R C, Wiman K G. The single stranded DNA end binding site of p53 coincides with the C-terminal regulatory region. Nucleic Acids Res 1996; 24: 3560-3567.

Yamamoto N. Damage, repair, and recombination. II. Effect of hydrogen peroxide on the bacteriophage genome. Virology 1969; 38: 457-463. Zhang X, San Gabriel M, Libman J, Phillips S, Courchesne A, Zini A. Localization of single-stranded DNA in human sperm nuclei. Fertil Steril 2007; 88: 1334-1338.

Zini A, Sigman M. 2009. Are tests of sperm DNA damage clinically useful? Pros and cons. J Androl 2009; 30: 219-229.

SEQUENCE LISTING

```
<160> NUMBER OF SEQ ID NOS: 2

<210> SEQ ID NO 1
<211> LENGTH: 22
<212> TYPE: PRT
<213> ORGANISM: Homo sapiens

<400> SEQUENCE: 1

Gly Ser Arg Ala His Ser Ser His Leu Lys Ser Lys Lys Gly Gln Ser
1               5                   10                  15

Thr Ser Arg His Lys Lys
            20

<210> SEQ ID NO 2
<211> LENGTH: 10
<212> TYPE: PRT
<213> ORGANISM: Homo sapiens

<400> SEQUENCE: 2

Lys Gly Gln Ser Arg Ser Arg His Lys Lys
1               5                   10
```

Singh N P, McCoy M T, Tice R R, Schneider E L. A simple technique for quantitation 901 of low levels of DNA damage in individual cells. Exp Cell Res 1988; 175: 184-191.

Spano M, Bonde J, Hjollund H, Kolstad H, Cordelli E, Leter G. Sperm chromatin damage impairs human fertility. Fertil Steril 2000; 73: 43-50.

Virro M, Larson-Cook K, Evenson D. Sperm chromatin structure assay (SCSAR) parameters are related to fertilisation, blastocyst development, and ongoing pregnancy in in vitro fertilisation and intracytoplasmic sperm injection cycles. Fertil Steril 2004; 81: 1289-1295.

Vogelstein B, Lane D, Levine A J. Surfing the p53 network. Nature 2000; 408: 307-310.

Vousden K H, Lane D P. p53 in health and disease. Nat Rev Mol Cell Biol 2007; 8: 275-283.

Vousden K H, Lu X. Live or let die: the cell's response to p53. Nat Rev Cancer 2002; 2: 594-604.

WHO: World Health Organization, Department of Reproductive Health and Research. WHO Laboratory Manual for the Examination and Processing of Human Semen, 5th edn, 2010. WHO Press, Geneva, Italy.

Wu L, Bayle J H, Elenbaas B, Pavletich N P, Levine A J. Alternatively spliced forms in the carboxy terminal domain of the p53 protein regulate its ability to promote annealing of complementary single strands of nucleic acids. Mol Cell Biol 1995; 15: 497-504.

Wyrobek A J, Eskenazi B, Young S, Arnheim N, Tiemann-Boege I, Jabs E W, Glaser 925 RL, Pearson F S, Evenson D. Advancing age has differential effects on DNA damage, chromatin integrity, gene mutations, and aneuploidies in sperm. Proc Natl Acad Sci USA 2006; 103: 9601-9606.

What is claimed is:

1. A ssDNA binding peptide comprising the sequence of SEQ ID NO:2.

2. The peptide of claim 1, further comprising an attached chromophore.

3. A viable sperm determining kit comprising Annexin V and a ssDNA and fragmented DNA binding peptide comprising the peptide of SEQ ID NO:2.

4. A method of detecting viable sperm comprising the steps of:
   a) staining sperm with chromophore labeled Annexin V and,
   b) staining sperm with a different chromophore labeled peptide of SEQ ID 2 and,
   c) identifying those sperm not stained which are viable.

5. A method of detecting viable sperm comprising the steps of:
   a) staining the sperm with a dye selected from Hoecht, DAPI, and Sytox Green to determine viability, and
   b) staining additionally with the peptide of SEQ ID NO:2; and,
   c) identifying those viable sperm which do not stain with the peptide of SEQ ID NO:2.

6. A method of intracytoplasmic sperm injection comprising
   a) adding a peptide of claim 2 to human sperm and,
   b) removing microsurgically a non-stained human sperm; and,
   c) inserting said non-stained human sperm into an oocyte.

* * * * *